US010011611B2

(12) United States Patent
Ma et al.

(10) Patent No.: US 10,011,611 B2
(45) Date of Patent: Jul. 3, 2018

(54) HISTONE DEACETYLASE INHIBITORS AND METHODS FOR USE THEREOF

(71) Applicant: Reaction Biology Corp., Malvern, PA (US)

(72) Inventors: Haiching Ma, Malvern, PA (US); Yuren Wang, Washington Crossing, PA (US)

(73) Assignee: REACTION BIOLOGY CORP., Malvern, PA (US)

( * ) Notice: Subject to any disclaimer, the term of this patent is extended or adjusted under 35 U.S.C. 154(b) by 0 days.

(21) Appl. No.: 15/234,412

(22) Filed: Aug. 11, 2016

(65) Prior Publication Data
US 2017/0044185 A1    Feb. 16, 2017

Related U.S. Application Data

(60) Provisional application No. 62/205,056, filed on Aug. 14, 2015.

(51) Int. Cl.
| C07D 513/04 | (2006.01) |
| A61K 31/437 | (2006.01) |
| A61K 45/06 | (2006.01) |
| C07D 409/12 | (2006.01) |
| A61K 31/4436 | (2006.01) |
| C07D 213/82 | (2006.01) |
| A61K 31/44 | (2006.01) |

(52) U.S. Cl.
CPC .......... *C07D 513/04* (2013.01); *A61K 31/437* (2013.01); *A61K 31/44* (2013.01); *A61K 31/4436* (2013.01); *A61K 45/06* (2013.01); *C07D 213/82* (2013.01); *C07D 409/12* (2013.01)

(58) Field of Classification Search
None
See application file for complete search history.

(56) References Cited

U.S. PATENT DOCUMENTS

| 6,214,857 B1 | 4/2001 | Muller et al. |
| 8,748,451 B2 | 6/2014 | Kozikowski et al. |
| 9,745,253 B2 | 8/2017 | Bair et al. |

(Continued)

FOREIGN PATENT DOCUMENTS

| DE | 19533643 A1 | 3/1997 |
| EP | 0429240 | 5/1991 |

(Continued)

OTHER PUBLICATIONS

Gentile et al., Curr Drug Targets CNS Neurol Disord. Apr. 2004; 3(2):99-104.*

(Continued)

*Primary Examiner* — Karl J Puttlitz
(74) *Attorney, Agent, or Firm* — Riverside Law LLP

(57) ABSTRACT

The present invention relates to methods of modulating (for example inhibiting) activity of histone deacetylases (HDACs) and/or treating HDACs-associated diseases including, for example, cancers, inflammatory disorders, neurodegenerative disorders, etc. The invention also provides novel compounds and compositions thereof, methods of preparation of the same, as well as methods of use of the same for inhibition of HDACs and/or treatment of HDAC-associated diseases.

14 Claims, 5 Drawing Sheets

(56) References Cited

U.S. PATENT DOCUMENTS

| | | | |
|---|---|---|---|
| 9,765,066 | B2 | 9/2017 | van Duzer et al. |
| 2004/0087558 | A1 | 5/2004 | Zeldis |
| 2004/0091454 | A1 | 5/2004 | Zeldis |
| 2004/0175382 | A1 | 9/2004 | Schafer |
| 2005/0239867 | A1 | 10/2005 | Zeldis |
| 2007/0099970 | A1 | 5/2007 | Mackerell et al. |
| 2007/0207121 | A1 | 9/2007 | Zeldis |
| 2008/0300268 | A1 | 12/2008 | Singh et al. |
| 2009/0005422 | A1 | 1/2009 | Holmgren et al. |
| 2009/0226422 | A1 | 9/2009 | Chaudhary et al. |
| 2009/0312377 | A1 | 12/2009 | Gomez Vidal et al. |
| 2009/0325944 | A1 | 12/2009 | Walker Kahne et al. |
| 2013/0224259 | A1 | 8/2013 | Ghebremariam et al. |
| 2014/0296169 | A1 | 10/2014 | Szillat et al. |

FOREIGN PATENT DOCUMENTS

| | | | |
|---|---|---|---|
| EP | 0542463 | | 5/1993 |
| WO | 9906041 | | 2/1999 |
| WO | 02085883 | A1 | 10/2002 |
| WO | 03097040 | A1 | 11/2003 |
| WO | 2004034962 | A2 | 4/2004 |
| WO | 2004037207 | A2 | 5/2004 |
| WO | 2004043336 | A2 | 5/2004 |
| WO | 2004043378 | A2 | 5/2004 |
| WO | 2005043971 | A2 | 5/2005 |
| WO | 2005046592 | A2 | 5/2005 |
| WO | 2005110085 | A2 | 11/2005 |
| WO | 2005112917 | A1 | 12/2005 |
| WO | 2005112918 | A1 | 12/2005 |
| WO | 2006050057 | A2 | 5/2006 |
| WO | 2006065814 | A1 | 6/2006 |
| WO | 2008003800 | | 10/2008 |
| WO | 2009158369 | A1 | 12/2009 |
| WO | 2010039534 | A2 | 4/2010 |
| WO | 2010039545 | A2 | 4/2010 |
| WO | 2010093588 | A1 | 8/2010 |
| WO | 2011127019 | A2 | 10/2011 |
| WO | 2013025897 | A1 | 2/2013 |
| WO | 2013/092574 | * | 6/2013 |
| WO | 2013092574 | A1 | 6/2013 |
| WO | 20140160947 | A1 | 10/2014 |

OTHER PUBLICATIONS

Eckert et al., Mol Carcinog. Oct. 2015;54(10):947-58.*

Valente & Mai, "Small-molecule inhibitors of histone deacetylase for the treatment of cancer and non-cancer diseases: a patent review (2011-2013)". 2014, Expert Opin. Ther. Patents, 24:1-15.

Carmi et al., "Novel Irreversible Epidermal Growth Factor Receptor Inhibitors by Chemical Modulation of the Cysteine-Trap Portion". 2010, J. Med. Chem. 53:2038-2050.

Csakai et al., "Saccharin Derivatives as Inhibitors of Interferon-Mediated Inflammation". 2014, J. Med. Chem., 57:5348-5355.

Furdas et al., "Pyrido- and benzisothiazolones as inhibitors of histone acetyltransferases (HATs)". 2014, Med. Chem. Commun, 5:1856-1862.

Furdas et al., "Synthesis and biological testing of novel pyridoisothiazolones as histone acetyltransferase inhibitors". 2011, Bioorg. Med. Chem. 19:3678-3689.

Gorsuch et al., "Synthesis of isothiazol-3-one derivatives as inhibitors of histone actetyltransferases (HATs)". 2009, Bioorg. Med. Chem. 17:467-474.

H. Lee Moffitt Cancer Center and Research Institute et al, "Phase I of Histone Deacetylase (HDAC) Inhibitor Panobinostat With Ipilimumab With Unresectable III/IV Melanoma". 2017, ClinicalTrials.gov, 1-3. <https://clinicaltrials.gov/beta/show/NCT02032810?term=nct02032810&>.

University of Aarhus et al., "Safety and Effect of the HDAC Inhibitor Panobinostat on HIV-1 Expression in Patients on Suppressive HART (CLEAR)". 2014, ClinicalTrials.gov, 1-3. <https://clinicaltrials.gov/beta/show/NCT01680094?term=nct01680094&>.

All India Institute of Medical Sciences, New Delhi, "Valproate and Levocarnitine in Children With Spinal Muscular Atrophy". 2015, ClinicalTrials.gov, 1-3. <https://clinicaltrials.gov/beta/show/NCT01671384?term=nct01671384&>.

University of North Carolina, Chapel Hill et al., "The Effect of Vorinostat on HIV RNA Expression in the Resting CD4+ T Cells of HIV+ Pts on Stable ART". 2016, ClinicalTrials.gov, 1-3. <https://clinicaltrials.gov/beta/show/NCT01319383?term=nct01319383&>.

Bayside Health et al., "Safety and Effect on HIV Transcription of Vorinostat in Patients Receiving Suppressive Combination Antiretroviral Therapy". 2017, ClinicalTrials.gov, 1-3. <https://clinicaltrials.gov/beta/show/NCT01365065?term=nct01365065&>.

Wright et al., "Metabolism Resistant Isothiazolone Inhibitors of Cartilage Breakdown". 1995, Bioorg. Med. Chem. 3:227-234.

Gallinari et al., "HDACs, histone deacetylation and gene transcription: from molecular biology to cancer therapeutics". 2007, Cell Res. 17:191-211.

Kazantsev and Thompson, "Therapeutic application of histone deacetylase inhibitors for central nervous system disorders", 2008, Nat Rev Drug Discov. 7:854-868.

Falkenberg and Johnstone, "Histone deacetylases and their inhibitors in cancer, neurological diseases and immune disorders", 2014, Nat Rev Drug Discov. 13:673-91.

Bots & Johnstone, "Rational Combinations Using HDAC Inhibitors", 2009. Clin. Cancer Res. 15, 3970-3977.

Weber DM, et al., "Phase I Trial of Vorinostat Combined With Bortezomib for the Treatment of Relapsing and/or Refractory Multiple Myeloma", 2012, Clin. Lymphoma Myeloma Leuk. 12, 319-324.

Santo L, et al, "Preclinical activity, pharmacodynamic, and pharmacokinetic properties of a selective HDAC6 inhibitor, ACY-1215, in combination with bortezomib in multiple myeloma", 2012, Blood.; 119: 2579-2589.

Hu et al., "Identification of Novel Isoform-Selective Inhibitors within Class I Histone Deacetylases", 2003, J Pharmacol. Ther. 307: 720-728.

Giannini et et al., "Histone deacetylase inhibitors in the treatment of cancer: overview and perspectives", 2012, Future Med Chem. 4:1439-1460.

Weïwer et al., "Therapeutic potential of isoform selective HDAC inhibitors for the treatment of schizophrenia", 2013, Future Med Chem. 5:1491-1508.

Blackwell et al., "The use of diversity profiling to characterize chemical modulators of the histone deacetylases", 2008, Life Sciences 82:1050-1058.

Shankar and Sirvastava, "Histone Deacetylase Inhibitors: Mechanisms and Clinical Significance in Cancer", 2008, Adv Exp Med Biol 615:261-298.

Parmigiani et al., "HDAC6 is a specific deacetylase of peroxiredoxins and is involved in redox regulation", 2008, PNAS 105:9633-9638.

Nakagawa et al. "Expression profile of class I histone deacetylases in human cancer tissues", 2007, Oncol Rep, 18:769-774.

Oehme et al., "Histone Deacetylase 8 in Neuroblastoma Tumorigenesis", 2009, Clin Cancer Res, 15:91-99.

Mottamal M et al., "Histone Deacetylase Inhibitors in Clinical Studies as Templates for New Anticancer Agents", 2015, Molecules 20:3898-3941.

Guan JS et al., "HDAC2 negatively regulates memory formation and synaptic plasticity", 2009, Nature, 459: 55-60.

Akhtar MW et al, "Histone Deacetylases 1 and 2 Form a Developmental Switch That Controls Excitatory Synapse Maturation and Function", 2009, J. Neurosci, 29:8288-8297.

McQuown SC et al., "Epigenetic Regulation in Substance Use Disorders", 2010, Curr. Psychiatr. Rep.,12:145-153.

Morris MJ Et al, "Loss of histone deacetylase 2 improves working memory and accelerates extinction learning", 2013, J. Neurosci., 33:6401-6411.

Graff J et al., "An epigenetic blockade of cognitive functions in the neurodegenerating brain", 2012, Nature, 483:222-226.

Graff J. Et al., "Epigenetic Priming of Memory Updating during Reconsolidation to Attenuate Remote Fear Memories", 2014, Cell 156:261-276.

(56) References Cited

OTHER PUBLICATIONS

Villalba et al., "Sirtuin activators and inhibitors", 2012, 38(5):349-59.
Chen L, "Medicinal chemistry of sirtuin inhibitors", Curr Med Chem. 2011; 18(13):1936-46.
Gregoretti et al., "Molecular Evolution of the Histone Deacetylase Family: Functional Implications of Phylogenetic Analysis," 2004, J. Mol. Biol. 338:17-31.
Grozinger and Schreiber, Deacetylase Enzymes: Biological Functions Review and the Use of Small-Molecule Inhibitors, 2002, Chem. & Biol. 9:3-16.
Thurn et al., "Rational therapeutic combinations with histone deacetylase inhibitors for the treatment of cancer," 2011, Future Onc. 7:263-283.

\* cited by examiner

Compound RBC-3001-B biochemical activity:

| Compound ID | HDAC1 IC50 (M) | HDAC2 IC50 (M) | HDAC3 IC50 (M) | HDAC4 IC50 (M) | HDAC5 IC50 (M) | HDAC6 IC50 (M) | HDAC7 IC50 (M) | HDAC8 IC50 (M) | HDAC9 IC50 (M) | HDAC10 IC50 (M) | HDAC11 IC50 (M) |
|---|---|---|---|---|---|---|---|---|---|---|---|
| RBC-3001-B | 1.40E-06 | 3.99E-06 | 2.04E-06 | 9.23E-06 | 3.97E-06 | 1.30E-09 | 2.78E-06 | 1.54E-07 | 2.26E-06 | 4.52E-06 | 9.01E-06 |
| Trichostatin A | 9.55E-09 | 2.10E-08 | 1.56E-08 | ND | ND | 2.85E-09 | ND | 5.20E-07 | ND | 5.02E-08 | 3.81E-06 |
| TMP269 | ND | ND | ND | 3.72E-07 | 4.59E-07 | ND | 1.15E-07 | ND | 2.78E-08 | ND | ND |

HISTONE DEACETYLASE INHIBITORS AND METHODS FOR USE THEREOF

CROSS-REFERENCE TO RELATED APPLICATIONS

This application claims priority from U.S. Provisional Patent Application Ser. No. 62/205,056, filed Aug. 14, 2015, the entire contents of which is incorporated herein by reference.

BACKGROUND OF THE INVENTION

Histone deacetylase (HDAC) proteins are a family of enzymes that control the acetylation state of protein lysine residues, notably lysine residues contained in the N-terminal extensions of core histones. The acetylation state of histones affect gene expression by influencing chromatin conformation. In addition, the stability or biological function of several non-histone proteins is regulated by the acetylation state of specific lysine residues (Gallinari et al., 2007, Cell Res. 17:191-211; Kazantsev and Thompson, 2008, Nat Rev Drug Discov. 7:854-868).

In humans, HDAC proteins comprise a family of 18 members, which are separated into four classes based on size, cellular localization, number of catalytic active sites, and homology to yeast HDAC proteins. Class I includes HDAC1, HDAC2, HDAC3, and HDAC8. Class II consists of six HDAC proteins that are further divided into two subclasses. Class IIa includes HDAC4, HDAC5, HDAC7, and HDAC9, which each contain a single catalytic active site. Class IIb includes HDAC6 and HDAC10, which each contain two active sites, although only HDAC6 has two catalytically competent active sites. HDAC11 is the sole member of class IV, based on phylogenetic analysis. Class I, II, and IV HDAC proteins operate by a metal ion-dependent mechanism, as indicated by crystallographic analysis. In contrast, class III HDAC proteins, referred to as sirtuins (i.e., SIRT1 through SIRT7), operate by a $NAD^+$-dependent mechanism unrelated to the other HDAC proteins (Gregoretti et al., 2004, J Mol Biol. 338:17-31; Grozinger and Schreiber, 2002, Chem Biol. 9:3-16).

The overexpression of different isoforms of HDACs has been found in several types of cancers, as well as in neurological and inflammatory pathologies. The use of HDAC inhibitors represents a treatment for such diseases (Valente and Mai, 2014, Expert Opin. Ther. Patents, 24:1-15; Falkenberg and Johnstone, 2014, Nat Rev Drug Discov. 13:673-91). The following are examples of HDAC inhibitors that have been tested in clinical trials both as single agents and in combination with chemotherapies and other targeted therapeutics: ACY1215 (Acetylon), CG200745 (Crystal Genomics), 4SC-202 (4SC corporation), CHR-2845 (Chroma Therapeutics), AR-42 (Arno Therapeutics), CUDC-101 (Curis Inc), Givinostat (Italfarmaco), Resminostat (4SC-Corporation), Pracinostat (S*BIO Pte Ltd), Etinostat (Syndax), Abexinostat (Pharmacyclics), Mocetinostat (Methylgene), Belinostat (TopoTarget), Valproic Acid (Instituto Nacional de Cancerologia), Panobinostat (Novartis), Vorinostat (Merck), and Romidepsin (Celgene).

HDAC inhibitors have been combined with a broad range of agents (Bots, & Johnstone, 2009. Clin. Cancer Res. 15, 3970-3977). The most prominent example of the empirical testing of HDAC inhibitors in combination is with DNA-damaging chemotherapeutics, which have led to many successful outcomes (Thum, et al, 2011, Future Oncol. 7, 263-283). HDAC inhibitors have also been successfully combined with DNMT inhibitors. Two Phase I trials have been carried out with vorinostat and bortezomib for the treatment of relapsing and/or refractory multiple myeloma with overall positive responses (Weber D M, Graef T et al 2012, Clin. Lymphoma Myeloma Leuk. 12, 319-324). A Phase III trial is currently assessing VPA (Valproic acid) in combination with levocamitine in children with spinal muscular atrophy (ClinicalTrials.gov identifier: NCT01671384). Vorinostat, panobinostat and VPA are currently being tested in combination with various antiretroviral therapies (ClinicalTrials.gov identifiers: NCT01680094, NCT01319383 and NCT01365065). A Phase I study combining Panobinostat with Ipilimumab to treat unresectable III/IV melanoma has just started (ClinicalTrials.gov identifiers: NCT02032810). HDAC6-specific inhibitors, rocilinostat (ACY-1215), is being tested clinically for the treatment of multiple myeloma in combination with bortezomib, following promising preclinical results (Santo L, Hideshima T, et al, 2012. Blood; 119: 2579-2589.).

Many of the earlier HDAC inhibitors tested in clinical trials are either pan-inhibitors or have poor isoform selectivity. Thus, there is an interest in identifying HDAC inhibitors exhibiting selectivity within or between the human HDAC isoform classes. Achieving selectivity would not only reduce side effects, but would also provide the ability to target distinct therapeutic areas (Hu et al., 2003, J Pharmacol. Ther. 307: 720-728; Giannini et al., 2012, Future Med Chem. 4:1439-1460; Weïwer et al., 2013, Future Med Chem. 5:1491-1508; Falkenberg and Johnstone, 2014, Nat Rev Drug Discov. 13:673-91).

HDAC6 is a well-characterized class IIb deacetylase that regulates many important biological processes via the formation of complexes with its partner proteins. HDAC6 possesses two catalytic domains and a C-terminal zinc finger domain (ZnF-UBP domain, also known as BUZ) that binds free ubiquitin, as well as mono and polyubiquitinated proteins, with high affinity. HDAC6 is localized predominantly in the cytoplasm, and has been reported as a tubulin deacetylase that has effects on microtubule (MT)-mediated processes through both deacetylase-dependent and deacetylase-independent mechanisms. HDAC6 is important both for cytoplasmic and nuclear functions. Unlike other deacetylases, HDAC6 has unique substrate specificity for non-histone proteins such as α-tubulin, HSP90, cortactin, peroxiredoxins, chaperone proteins, β-Catenin, and hypoxia inducible factor-1α (HIF-1α) (Blackwell et al., 2008, Life Science 82:1050-1058; Shnakar and Sirvastava, 2008, Adv Exp Med Biol 615:261-298). HDAC6 also deacetylates protein peroxiredoxins, which are proteins critical in protecting cells from the oxidative effects of $H_2O_2$ (Parmigiani et al., 2008, PNAS 105:9633-9638). However, HDAC6 does not catalyze histone deacetylation in vivo. Therefore, it is a safer drug target since it does not impact DNA biology. As a MT-mediated cytoplasmic enzyme, HDAC6, through complexes with partner proteins, regulates multiple important biological processes, such as cell migration, cell spreading, immune synapse formation, viral infection, the degradation of misfolded proteins and stress granule (SG) formation. Mice lacking HDAC6 are viable and have greatly elevated tubulin acetylation in multiple organs. In addition, mice lacking HDAC6 exhibit a moderately impaired immune response and bone homeostasis. Such diverse functions of HDAC6 suggest that HDAC6 serves a potential therapeutic target for the treatment of a wide range of diseases. HDAC6 selective inhibitors have been tested in preclinical indications for cancers, neurology, inflammation, Gaucher's disease, Parkinson's disease, Huntington's disease; Alzheimer's diseases, depression and anxiety, and pain etc. (Gianniniet et al., 2012, Future Med Chem. 4:1439-1460; Falkenberg and Johnstone, 2014, Nat Rev Drug Discov. 13:673-91;).

HDAC8, on the basis of sequence homology, is considered to be a class I enzyme, although phylogenetic analysis has shown it to lay near the boundary of the class I and class II enzymes. HDAC8's importance has been revealed by knockdown experiments of selective HDAC isoforms showing it as essential for cell survival. HDAC8 specific inhibition selectively induces apoptosis in T-cell derived lymphoma and leukemic cells The expression of HDAC8 has been described in a variety of cancer entities e.g. colon, breast lung, pancreas and ovary cancer (Nakagawa et al. 2007, Oncol Rep, 18:769-774). In the highly malignant childhood cancer neuroblastoma high HDAC8 expression significantly correlates with poor prognostic markers and poor overall and event-free survival. In cultured neuroblastoma cells knockdown and pharmacological inhibition of HDAC8 resulted in inhibition of proliferation, reduced clonogenic growth, cell cycle arrest and differentiation (Oehme et al. 2009, Clin Cancer Res, 15:91-99). Furthermore, HDAC8 promotes lung, colon and cervical cancer cell proliferation and may regulate telomerase activity. The three dimensional crystal structure of human HDAC8 was the first to be solved, and 14 human HDAC8 structures co-crystallized with different inhibitors have been described. Currently, HDAC 8 selective inhibitors are in preclinical trials for cancer (Giannini G et al., 2012, Future Med Chem. 4:1439-1460; Falkenberg and Johnstone, 2014, Nat Rev Drug Discov. 13:673-91). Thus, there remains a need in the art for inhibitors of HDACs having high selectivity within and between various HDAC classes, which can serve as therapeutic agents against a variety of diseases and disorders. The present invention fulfills this need.

Class I HDACs, including HDAC1, HDAC2, HDAC3 and HDAC8, are regulating cell survival and proliferation, which makes them ideal target for a variety of cancer types. In addition, HDAC1, HDAC2 and HDAC3 play important roles in regulating learning and memories (Mottamal M et al., 2015, Molecules 20:3898-3941). HDAC2 negatively regulates learning and memory (Guan J S et al., 2009, Nature, 459: 55-60). In mature neurons, the upregulated level of HDAC2 affects the basic excitatory neurotransmission, implying that HDAC2 plays a role in synaptic plasticity (Akhtar M W et al, 2009, J. Neurosci, 29:8288-8297). Knockout and/or over-expression transgenic mouse models of HDAC2, HDAC3 and HDAC6 have demonstrated that loss of function of these individual isoforms can enhance memory and synaptic plasticity (Guan J S et al., 2009, Nature, 459: 55-60; McQuown S C et al., 2010, Curr. Psychiatr. Rep., 12:145-153; Morris M J Et al, 2013, J. Neurosci., 33:6401-6411). HDAC2 inhibitors have been evaluated as therapeutic agents for neurological disorders such as Alzheimer's, Parkinson's, PTSD (Post Traumatic Stress Disorder) etc. (Graff J et al, 2012, Nature, 483:222-226; Graff J. Et al, 2014, Cell 156:261-276).

Sirtuins 1-7 (SIRT1-7) belong to the third class of deacetylase enzymes, which are dependent on NAD(+) for activity. Sirtuins activity is linked to gene repression, metabolic control, apoptosis and cell survival, DNA repair, development, inflammation, neuroprotection, and healthy aging. Because sirtuins modulation could have beneficial effects on human diseases there is a growing interest in the discovery of small molecules modifying their activities. Sirtuin inhibitors with a wide range of core structures have been identified for SIRT1, SIRT2, SIRT3 and SIRT5 (splitomicin, sirtinol, AGK2, cambinol, suramin, tenovin, salermide, among others). SIRT1 inhibition has been proposed in the treatment of cancer, immunodeficiency virus infections, Fragile X mental retardation syndrome and for preventing or treating parasitic diseases, whereas SIRT2 inhibitors might be useful for the treatment of cancer and neurodegenerative diseases. (Villalba et al 2012, 38(5):349-59; Chen L, Curr Med Chem. 2011; 18(13):1936-46).

Thus, there remains a need in the art for inhibitors of HDACs having high selectivity within and between various HDAC classes, which can serve as therapeutic agents against a variety of diseases and disorders. The present invention fulfills this need.

SUMMARY OF THE INVENTION

In one aspect, the invention relates to a compound of Formula I-A, or Formula I-B, or a salt or solvate thereof:

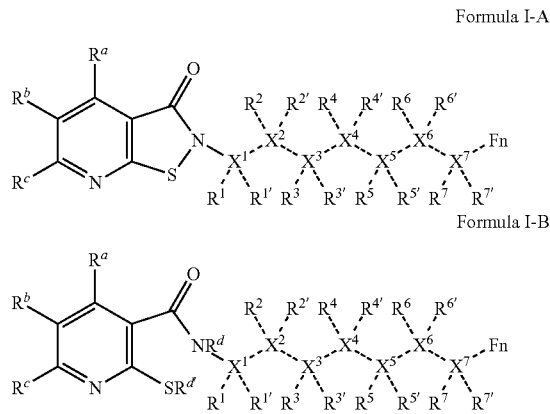

wherein in Formulae I-A and I-B:

$R^a$, $R^b$ and $R^c$ are each independently selected from the group consisting of H, F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, and wherein $R^d$, $R^{d'}$, $R^e$ and $R^f$ are each independently selected from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of $R^d$, $R^{d'}$, $R^e$ or $R^f$ can optionally be joined to form additional rings; and $R^a$, $R^b$ and $R^c$ can optionally be joined to form additional rings;

chain

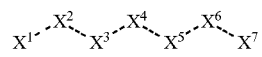

is an uninterrupted chain, wherein any bond can be a single, double or triple bond, consistent with the hybridization state of the connected atoms, and wherein a null selection for any of the $X^1$ to $X^7$ nodes results in a null selection for the adjacent R groups;

$X^1$, $X^2$, $X^3$, $X^4$, $X^5$, $X^6$, and $X^7$ are each independently selected from the group consisting of null, C, CH, CH$_2$, C(=O), O, N, NH, S, S(=O) and S(=O)$_2$;

$R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$ and $R^{7'}$ are each independently selected from the group consisting of null, H, F, Cl, Br, I, CN, NO$_2$, OR$^d$, OC(=O)R$^d$, OC(=O)OR$^d$, OC(=O)NR$^d$R$^e$, CR$^d$R$^e$R$^f$, CR$^d$R$^e$OR$^f$, C(=O)R$^d$, C(=O)NR$^d$R$^e$, C(=O)OR$^d$, NR$^d$R$^e$, NR$^d$C(=O)R$^e$, NR$^d$C(=O)OR$^e$, NR$^d$C(=O)NR$^e$R$^f$, NR$^d$S(=O)$_2$R$^e$, NR$^d$S(=O)$_2$NR$^e$R$^f$, SR$^d$, S(=O)R$^d$, S(=O)$_2$R$^d$, and S(=O)$_2$NR$^d$R$^e$, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, NO$_2$, OR$^d$, OC(=O)R$^d$, OC(=O)OR$^d$, OC(=O)NR$^d$R$^e$, CR$^d$R$^e$R$^f$, CR$^d$R$^e$OR$^f$, C(=O)R$^d$, C(=O)NR$^d$R$^e$, C(=O)OR$^d$, NR$^d$R$^e$, NR$^d$C(=O)R$^e$, NR$^d$C(=O)OR$^e$, NR$^d$C(=O)NR$^e$R$^f$, NR$^d$S(=O)$_2$R$^e$, NR$^d$S(=O)$_2$NR$^e$R$^f$, SR$^d$, S(=O)R$^d$, S(=O)$_2$R$^d$, and S(=O)$_2$NR$^d$R$^e$, and wherein R$^d$, R$^{d'}$, R$^e$ and R$^f$ are each independently selected from the group consisting of H, and optionally substituted C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of R$^d$, R$^{d'}$, R$^e$ or R$^f$ can optionally be joined to form additional rings; and any of R$^1$, R$^{1'}$, R$^2$, R$^{2'}$, R$^3$, R$^{3'}$, R$^4$, R$^{4'}$, R$^5$, R$^{5'}$, R$^6$, R$^{6'}$, R$^7$ and R$^{7'}$ can optionally be connected to each other to form various carbo- or heterocyclic systems; and Fn is selected from the group consisting of Formulae II, III, IV and V:

Formula II

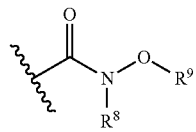

Formula III

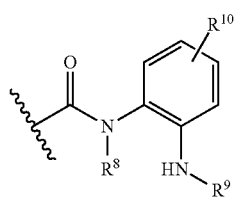

Formula IV

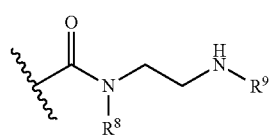

Formula V

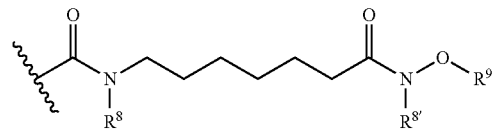

wherein in Formulae II, III, IV and V:

R$^8$, R$^{8'}$, R$^9$, and R$^{10}$ are each independently selected from the group consisting of null, H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, and R$^{10}$ can represent single, multiple, or no substitution.

In one embodiment, the compound of Formula I-A has a structure selected from the group consisting of Formulae VI-A, VII-A, VIII-A, IX-A, and X-A, or a salt or solvate thereof, and the compound of Formula I-B has a structure selected from the group consisting of Formulae VI-B, VII-B, VIII-B, IX-B, and X-B, or a salt or solvate thereof:

Formula VI-A

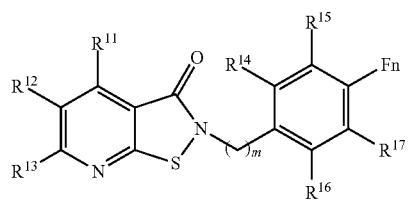

Formula VII-A

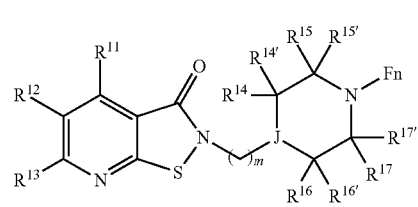

Formula VIII-A

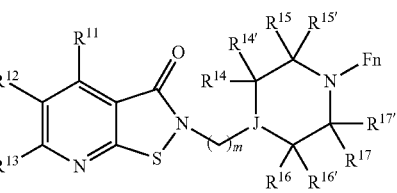

Formula IX-A

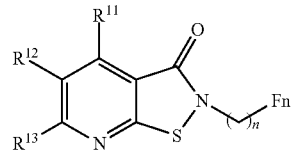

Formula X-A

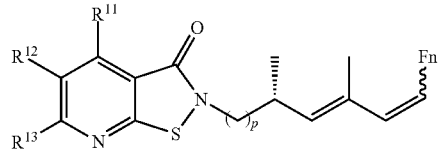

-continued

Formula VI-B
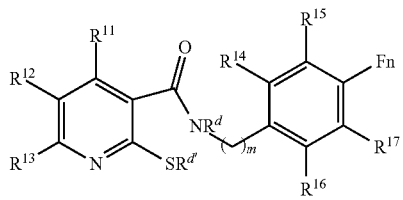

Formula VII-B
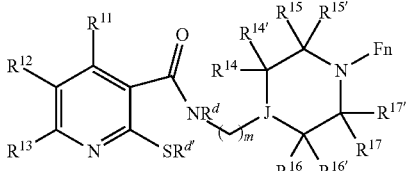

Formula VIII-B
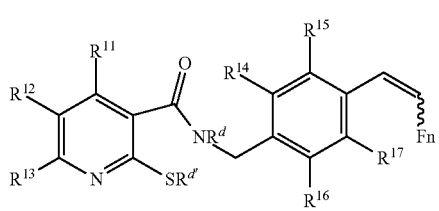

Formula IX-B
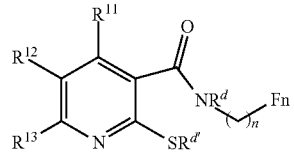

Formula X-B
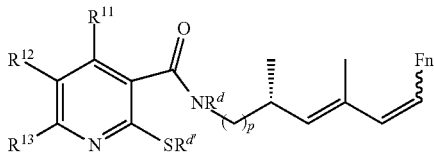

wherein in Formulae VI-A to X-B:

$R^{11}$, $R^{12}$, $R^{13}$, $R^{14}$, $R^{14'}$, $R^{15}$, $R^{15'}$, $R^{16}$, $R^{16'}$ $R^{17}$ and $R^{17'}$ are each independently selected from the group consisting of H, F, Cl, Br, I, CN, NO$_2$, OR$^d$, OC(=O)R$^d$, OC(=O)OR$^d$, OC(=O)NR$^d$R$^e$, CR$^d$R$^e$R$^f$, CR$^d$R$^e$OR$^f$, C(=O)R$^d$, C(=O)NR$^d$R$^e$, C(=O)OR$^d$, NR$^d$R$^e$, NR$^d$C(=O)R$^e$, NR$^d$C(=O)OR$^e$, NR$^d$C(=O)NR$^e$R$^f$, NR$^d$S(=O)$_2$R$^e$, NR$^d$S(=O)$_2$NR$^e$R$^f$, SR$^d$, S(=O)R$^d$, S(=O)$_2$R$^d$, and S(=O)$_2$NR$^d$R$^e$, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, NO$_2$, OR$^d$, OC(=O)R$^d$, OC(=O)OR$^d$, OC(=O)NR$^d$R$^e$, CR$^d$R$^e$R$^f$, CR$^d$R$^e$OR$^f$, C(=O)R$^d$, C(=O)NR$^d$R$^e$, C(=O) OR$^d$, NR$^d$R$^e$, NR$^d$C(=O)R$^e$, NR$^d$C(=O)OR$^e$, NR$^d$C(=O) NR$^e$R$^f$, NR$^d$S(=O)$_2$R$^e$, NR$^d$S(=O)$_2$NR$^e$R$^f$, SR$^d$, S(=O) R$^d$, S(=O)$_2$R$^d$, and S(=O)$_2$NR$^d$R$^e$, and wherein R$^d$, R$^{d'}$, R$^e$ and R$^f$ are each independently selected from the group consisting of H, and optionally substituted C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of R$^d$, R$^{d'}$, R$^e$ or R$^f$ can optionally be joined to form additional rings; and any of R$^{11}$, R$^{12}$, R$^{13}$, R$^{14}$, R$^{14'}$, R$^{15}$, R$^{15'}$, R$^{16}$, R$^{16'}$ R$^{17}$, and R$^{17'}$ can optionally be connected to each other to form various carbo- or heterocyclic rings;

m is an integer from 0 to 3, n is an integer from 0 to 7 and p is an integer from 0 to 2;

J is selected from the group consisting of CH and N; and

Fn is selected from the group consisting of Formulae II, III, IV and V:

Formula II
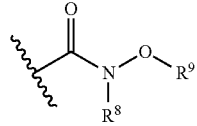

Formula III
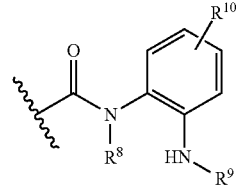

Formula IV
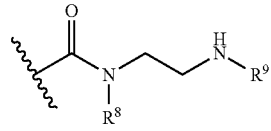

Formula V
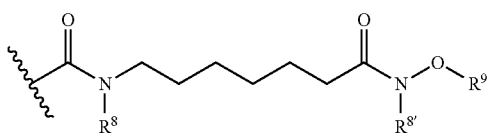

wherein in Formulae II, III, IV and V:

R$^8$, R$^{8'}$, R$^9$, and R$^{10}$ are each independently selected from the group consisting of null, H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, and R$^{10}$ can represent single, multiple, or no substitution.

In another embodiment, the compound has a chemical structure selected from the group consisting of RBC-1002a-A (N-(2-amino-4-(thiophen-2-yl)phenyl)-4-((3-oxoisothiazolo[5,4-b]pyridin-2(3H)-yl)methyl)benzamide), RBC-1002b-A (N-(2-amino-5-(thiophen-2-yl)phenyl)-4-((3-oxoisothiazolo[5,4-b]pyridin-2(3H)-yl)methyl)benzamide), RBC-3001-A (N-hydroxy-4-((3-oxoisothiazolo[5,4-b]pyridin-2(3H)-yl)methyl)benzamide), RBC-5001-A (N-(7-(hydroxyamino)-7-oxoheptyl)-4-((3-oxoisothiazolo[5,4-b] pyridin-2(3H)-yl)methyl)benzamide), RBC-7001-A (N-(2-aminophenyl)-4-((3-oxoisothiazolo[5,4-b]pyridin-2(3H)-yl)methyl)benzamide), RBC-1002a-B (N-(4-((2-amino-4-(thiophen-2-yl)phenyl)carbamoyl)benzyl)-2-mercaptonicotinamide), RBC-1002b-B (N-(4-((2-amino-5-(thiophen-2-yl)phenyl)carbamoyl)benzyl)-2-mercaptonicotinamide), RBC-3001-B (N-(4-(hydroxycarbamoyl)benzyl)-2-mercaptonicotinamide), RBC-5001-B (N-(4-((7-(hydroxyamino)-7-oxoheptyl)carbamoyl)benzyl)-2-mercaptonicotinamide, and RBC-7001-B (N-(4-((2-aminophenyl)carbamoyl)benzyl)-2-mercaptonicotinamide, or a salt or solvate thereof:

RBC-1002a-A

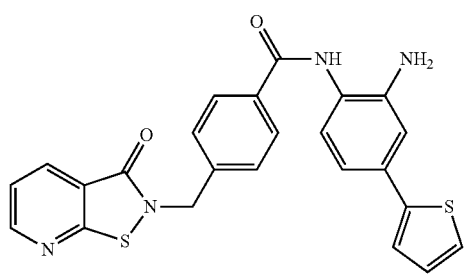

N-(2-amino-4-(thiophen-2-yl)phenyl)-
4-((3-oxoisothiazolo[5,4-b]pyridin-2
(3H)-yl)methyl)benzamide

RBC-7001-A

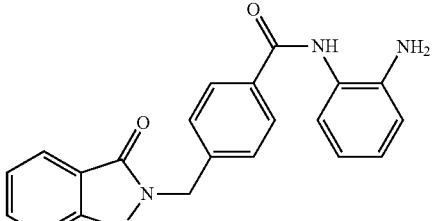

N-(2-aminophenyl)-
4-((3-oxoisothiazolo[5,4-b]pyridin-2
(3H)-yl)methyl)benzamide RBC-1002b-A

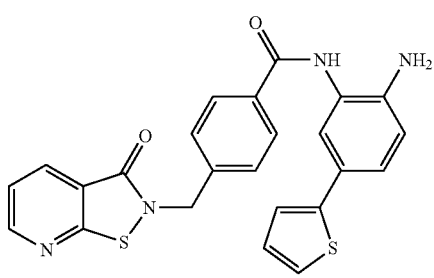

N-(2-amino-5-(thiophen-2-yl)phenyl)-
4-((3-oxoisothiazolo[5,4-b]pyridin-2
(3H)-yl)methyl)benzamide RBC-1002a-B

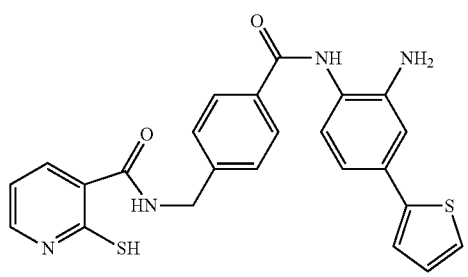

N-(4-((2-amino-4-(thiophen-2-yl)phenyl)
carbamoyl)benzyl)-2-mercaptonicotinamide

RBC-3001-A

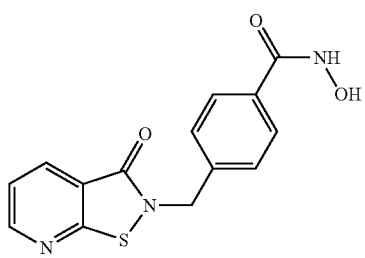

N-hydroxy-4-((3-oxoisothiazolo[5,4-b]pyridin-2
(3H)-yl)methyl)benzamide

RBC-1002-b-B

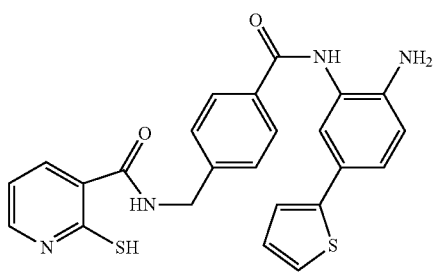

N-(4-((2-amino-5-(thiophen-2-yl)phenyl)
carbamoyl)benzyl-2-mercaptonicotinamide

RBC-5001-A

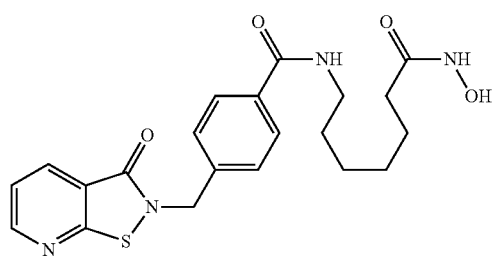

N-(7-(hydroxyamino)-7-oxoheptyl)-
4-((3-oxoisothiazolo[5,4-b]pyridin-2
(3H)-yl)methyl)benzamide

RBC-3001-B

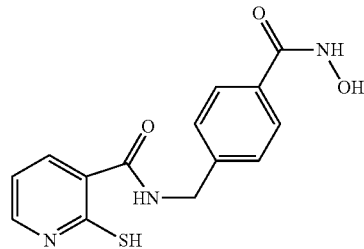

N-(4-(hydroxycarbamoyl)benzyl-2-
mercaptonicotinamide

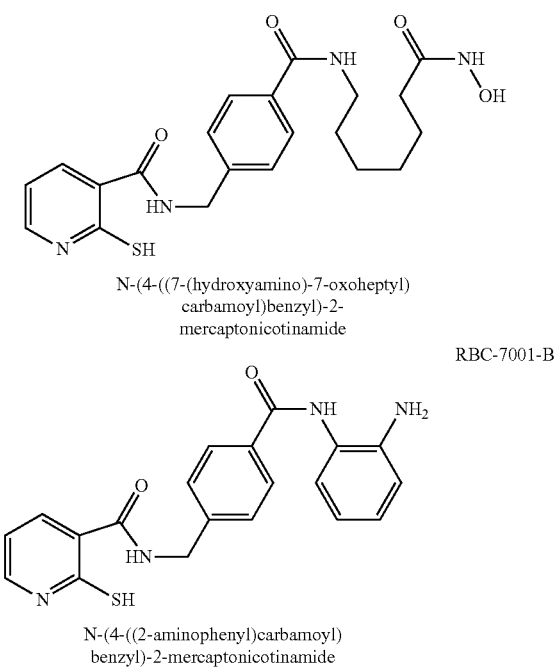

N-(4-((7-(hydroxyamino)-7-oxoheptyl)
carbamoyl)benzyl)-2-
mercaptonicotinamide

N-(4-((2-aminophenyl)carbamoyl)
benzyl)-2-mercaptonicotinamide

In another aspect, the invention relates to a composition comprising a compound of Formula I-A, and/or Formula I-B, or a salt or solvate thereof, and at least one pharmaceutically acceptable carrier.

In one aspect, the invention relates to a method of treating a disease or disorder associated with HDACs in a subject, the method comprising administering to the subject a therapeutically effective amount of a compound of Formula I-A, and/or a compound of Formula I-B, or a salt or solvate thereof. In one embodiment, the compound of Formula I-A has a chemical structure selected from the group consisting of Formulae VI-A, VII-A, VIII-A, IX-A, and X-A, or a salt or solvate thereof. In another embodiment, the compound of Formula I-B has a chemical structure selected from the group consisting of Formulae VI-B, VII-B, VIII-B, IX-B, and X-B, or a salt or solvate thereof. In another embodiment, the compound has a chemical structure selected from the group consisting of RBC-1002a-A (N-(2-amino-4-(thiophen-2-yl)phenyl)-4-((3-oxoisothiazolo[5,4-b]pyridin-2(3H)-yl)methyl)benzamide), RBC-1002b-A (N-(2-amino-5-(thiophen-2-yl)phenyl)-4-((3-oxoisothiazolo[5,4-b]pyridin-2(3H)-yl)methyl)benzamide), RBC-3001-A (N-hydroxy-4-((3-oxoisothiazolo[5,4-b]pyridin-2(3H)-yl)methyl)benzamide), RBC-5001-A (N-(7-(hydroxyamino)-7-oxoheptyl)-4-((3-oxoisothiazolo[5,4-b] pyridin-2(3H)-yl)methyl)benzamide), RBC-7001-A (N-(2-aminophenyl)-4-((3-oxoisothiazolo[5,4-b]pyridin-2(3H)-yl)methyl)benzamide), RBC-1002a-B (N-(4-((2-amino-4-(thiophen-2-yl)phenyl)carbamoyl)benzyl)-2-mercaptonicotinamide), RBC-1002b-B (N-(4-((2-amino-5-(thiophen-2-yl)phenyl)carbamoyl)benzyl)-2-mercaptonicotinamide), RBC-3001-B (N-(4-(hydroxycarbamoyl)benzyl)-2-mercaptonicotinamide), RBC-5001-B (N-(4-((7-(hydroxyamino)-7-oxoheptyl)carbamoyl)benzyl)-2-mercaptonicotinamide, and RBC-7001-B (N-(4-((2-aminophenyl)carbamoyl)benzyl)-2-mercaptonicotinamide, or a salt or solvate thereof.

In one embodiment, the compound selectively inhibits HDAC1. In another embodiment, the compound selectively inhibits HDAC2. In another embodiment, the compound selectively inhibits HDAC3. In another embodiment, the compound selectively inhibits HDAC4. In another embodiment, the compound selectively inhibits HDAC5. In another embodiment, the compound selectively inhibits HDAC6. In another embodiment, the compound selectively inhibits HDAC7. In another embodiment, the compound selectively inhibits HDAC8. In another embodiment, the compound selectively inhibits HDAC9. In another embodiment, the compound selectively inhibits HDAC10. In another embodiment, the compound selectively inhibits HDAC11. In another embodiment, the compound selectively inhibits SIRT1. In another embodiment, the compound selectively inhibits SIRT2. In another embodiment, the compound selectively inhibits SIRT3. In another embodiment, the compound selectively inhibits SIRT4. In another embodiment, the compound selectively inhibits SIRT5. In another embodiment, the compound selectively inhibits SIRT6. In another embodiment, the compound selectively inhibits SIRT7.

In one embodiment, the subject is a human. In another embodiment, the disease or disorder is cancer. In another embodiment, the disease or disorder is a psychiatric disease or disorder. In another embodiment, the disease or disorder is a neurologic disease or disorder. In another embodiment, the disease or disorder is a neurodegenerative disease or disorder. In another embodiment, the disease or disorder is a neuroinflammation disease or disorder. In another embodiment, the compound is administered to the subject orally, parenterally, intravascularly, intranasally, or intrabronchially.

In one embodiment, the method further comprises administering to the subject a therapeutically effective amount of an additional therapeutic agent for the treatment of a disease or disorder. In another embodiment, the additional therapeutic agent is selected from the group consisting of an immunomodulatory drug, an immunotherapeutic drug, a DNA-damaging chemotherapeutic, a proteasome inhibitor, an anti-androgen receptor, an antiretroviral drug, a reverse-transcriptase inhibitor, a chemotherapeutic drug, and an immunosuppressant.

In one aspect, the invention relates to a method of immunomodulation for organ transplant, the method comprising administering to a patient a therapeutically effective amount of a compound of Formula I-A, or a compound of Formula I-B, or both, or a salt or solvate thereof.

In another aspect, the invention relates to a kit for inhibiting an HDAC, comprising an amount of a compound of Formula I-A, or a compound of Formula I-B, or both, or a salt or solvate thereof, and an instruction manual for the use thereof.

In another aspect, the invention relates to a kit for treating a disease or disorder associated with an HDAC in a subject, comprising an amount of a compound of Formula I-A, or a compound of Formula I-B, or both, or a salt or solvate thereof, and an instruction manual for the use thereof.

In another aspect, the invention relates to a probe for imaging, diagnosing, or theragnosting a disease or disorder associated with an HDAC in a subject, comprising a compound of Formula I-A, or a compound of Formula I-B, or both, or a salt or solvate thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 4 depicts the results of exemplary experiments assessing the inhibitory activities of RBC-3001-B in biochemical HDAC assays. The IC50 values were calculated using the GraphPad Prism 4 program.

FIG. 5 depicts the results of exemplary experiments assessing the inhibitory activities of RBC-5001-A and RBC-7001-A in biochemical HDAC assays. The IC50 values were calculated using the GraphPad Prism 4 program.

DETAILED DESCRIPTION OF THE INVENTION

Figure 1:
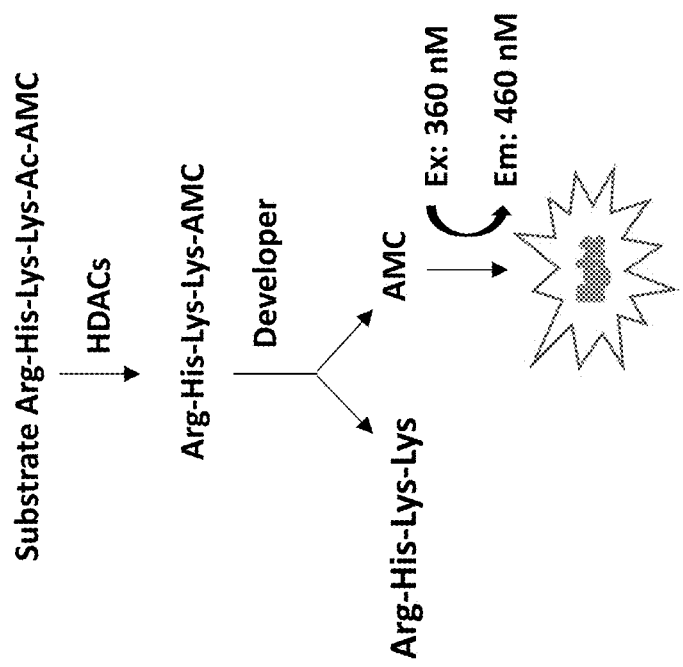
FIG. 1 depicts the HDAC Fluorescent Activity Assay, in which the deacetylation of a fluorogenic substrate by HDAC protein sensitizes it to the developer, which then generates a fluorophore having excitation at 360 nm light and emission at 460 nm, which is detected on a fluorometric plate reader.

The present invention provides novel compounds that are useful for modulating the activity of HDACs, and are potential therapeutics for various diseases and disorders, including but not limited to cancer, psychiatric disorders, neurologic disorders and neurodegenerative disorders, inflammation, virus infection, and bone and muscle-related disorders such as cancer-induced cachexia.

Definitions

As used herein, each of the following terms has the meaning associated with it in this section. Unless defined otherwise, all technical and scientific terms used herein generally have the same meaning as commonly understood by one of ordinary skill in the art to which this invention belongs. Generally, the nomenclature used herein and the laboratory procedures in biochemistry, analytical chemistry and organic chemistry are those well-known and commonly employed in the art. Standard techniques or modifications thereof are used for chemical syntheses and chemical analyses.

The articles "a" and "an" are used herein to refer to one or to more than one (i.e., to at least one) of the grammatical object of the article. By way of example, "an element" means one element or more than one element.

The term "about" as used herein when referring to a measurable value such as an amount, a temporal duration, and the like, is meant to encompass variations of +20% or +10%, more preferably +5%, even more preferably +1%, and still more preferably +0.1%

The terms "patient," "subject," "individual," and the like are used interchangeably herein, and refer to any animal, including mammals. In certain non-limiting embodiments, the patient, subject or individual is a human.

A "disease" is a state of health of an a subject wherein the subject cannot maintain homeostasis, and wherein if the disease is not ameliorated, the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health. As used herein, "treating a disease or disorder" means reducing the frequency and/or severity with which a symptom of the disease or disorder is experienced by an individual.

The term "treat," as used herein, means reducing the frequency and/or severity of a sign or symptom of a disease or disorder experienced by a subject. Thus, "treat" and "treating" are not limited to the case where the subject (e.g., patient) is cured and the disease or disorder is eradicated. Rather, the present invention also contemplates treatment that merely reduces signs or symptoms, improves (to some degree) and/or delays disease or disorder progression. The term "treatment" also refers to the alleviation, amelioration, and/or stabilization of signs or symptoms, as well as a delay in the progression of signs or symptoms of a disease or disorder. As used herein, to "alleviate" a disease or disorder means to reduce the frequency and/or severity of one or more signs and/or symptoms of the disease or disorder.

The term "effective amount" in a subject, as used herein, refers to an amount that provides a therapeutic or prophylactic benefit in the subject. The term "therapeutically effective amount" refers to the amount of the compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the signs and/or symptoms of the disease or disorder being treated. The therapeutically effective amount will vary depending on the compound, the disease or disorder, the severity of the disease or disorder, and the age, weight, etc., of the subject to be treated.

The term "pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or molecule useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound or molecule useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

As used herein, the term "composition" refers to a mixture of at least one compound or molecule useful within the invention with one or more different compound, molecule, or material. As used herein "pharmaceutical composition" or "pharmaceutically acceptable composition" refers to specific examples of compositions, wherein at least one compound or molecule useful within the invention is mixed with one or more pharmaceutically acceptable carriers. In some instances, the pharmaceutical composition facilitates administration of the compound or molecule to a patient. Multiple techniques of administering a compound or molecule exist in the art including, but not limited to, intravenous, oral, aerosol, parenteral, ophthalmic, pulmonary and topical administration.

As used herein, the term "alkyl," by itself or as part of another substituent means, unless otherwise stated, a straight or branched chain hydrocarbon having the number of carbon atoms designated (i.e., $C_1$-$C_6$ means one to six carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$) alkyl, particularly ethyl, methyl, isopropyl, isobutyl, n-pentyl, n-hexyl and cyclopropylmethyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e., skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

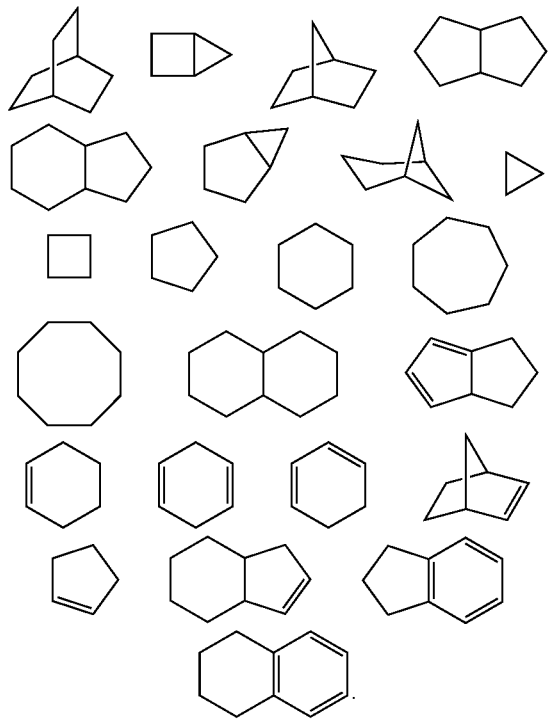

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbomane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

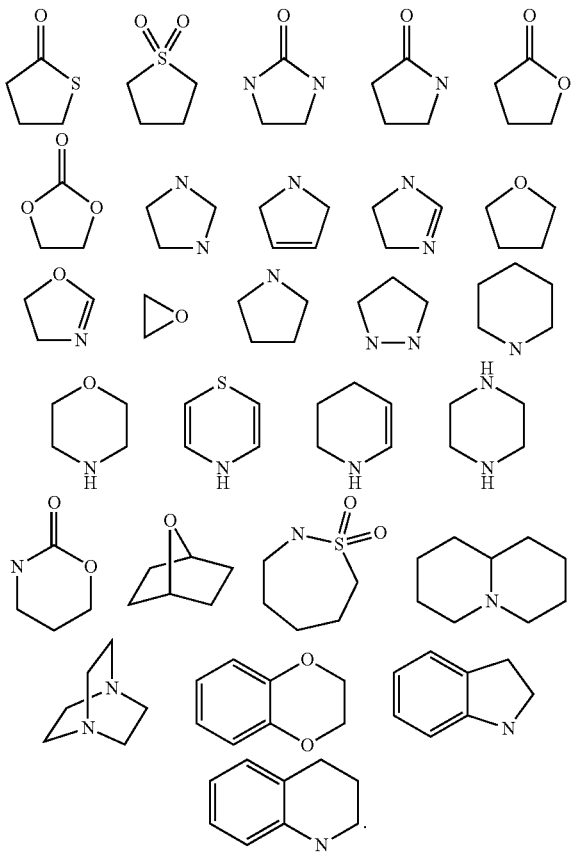

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term "heteroaryl" or "heteroaromatic" refers to a heterocycle having aromatic character. A polycyclic heteroaryl may include one or more rings that are partially saturated. Examples include the following moieties:

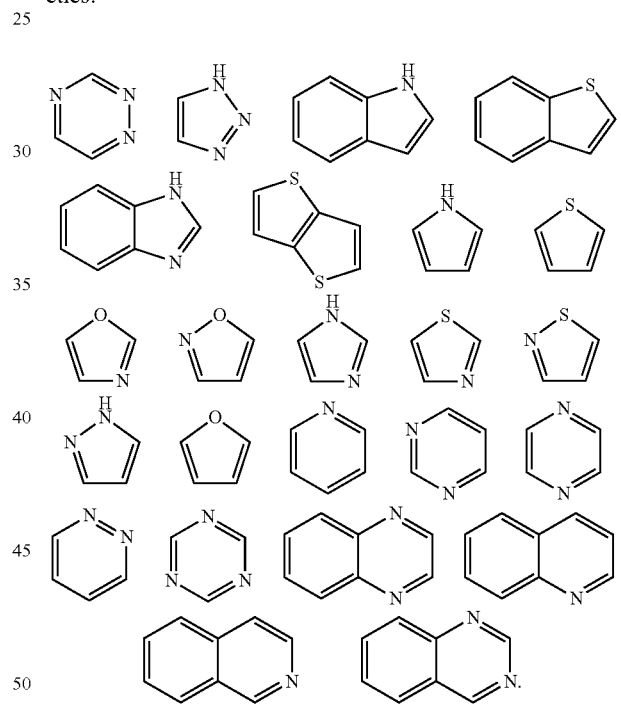

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or pentasubstitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C(NH$_2$)[substituted or unsubstituted alkyl]$_2$. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, and —C(=O)OH. In yet one embodiment, the substituents are independently selected from the group consisting of C$_{1-6}$ alkyl, —OH, C$_{1-6}$ alkoxy, halo, amino, acetamido, oxo and nitro. In yet another embodiment, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic, with straight being preferred.

As used herein, an "instructional material" or "instruction manual" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range and, when appropriate, partial integers of the numerical values within ranges. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range. Compounds of the Invention In one aspect, the invention relates to a compound with the chemical structure depicted in Formula I-A, or Formula I-B, or pharmaceutically acceptable salts thereof:

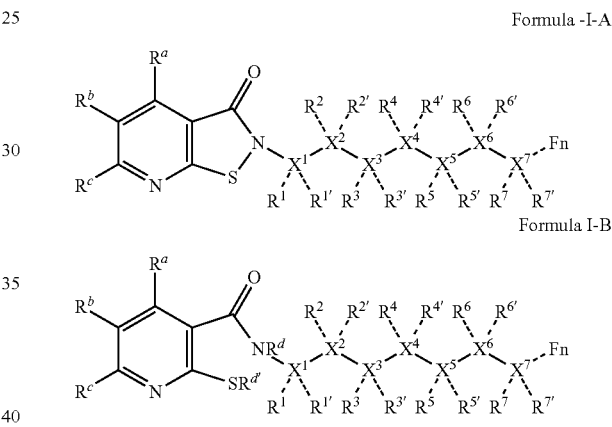

wherein in Formulae I-A and I-B:

$R^a$, $R^b$ and $R^c$ are each independently selected from the group consisting of H, F, Cl, Br, I, CN, NO$_2$, OR$^d$, OC(=O) R$^d$, OC(=O)OR$^d$, OC(=O)NR$^d$R$^e$, CR$^d$R$^e$R$^f$, CR$^d$R$^e$OR$^f$, C(=O)R$^d$, C(=O)NR$^d$R$^e$, C(=O)OR$^d$, NR$^d$R$^e$, NR$^d$C (=O)R$^e$, NR$^d$C(=O)OR$^e$, NR$^d$C(=O)NR$^e$R$^f$, NR$^d$S(=O)$_2$R$^e$, NR$^d$S(=O)$_2$NR$^e$R$^f$, SR$^d$, S(=O)R$^d$, S(=O)$_2$R$^d$, and S(=O)$_2$NR$^d$R$^e$, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, NO$_2$, OR$^d$, OC(=O)R$^d$, OC(=O) OR$^d$, OC(=O)NR$^d$R$^e$, CR$^d$R$^e$R$^f$, CR$^d$R$^e$OR$^f$, C(=O)R$^d$, C(=O)NR$^d$R$^e$, C(=O)OR$^d$, NR$^d$R$^e$, NR$^d$C(=O)R$^e$, NR$^d$C (=O)OR$^e$, NR$^d$C(=O)NR$^e$R$^f$, NR$^d$S(=O)$_2$R$^e$, NR$^d$S(=O)$_2$NR$^e$R$^f$, SR$^d$, S(=O)R$^d$, S(=O)$_2$R$^d$, and S(=O)$_2$NR$^d$R$^e$, and wherein R$^d$, R$^{d'}$, R$^e$ and R$^f$ are each independently selected from the group consisting of H, and optionally substituted C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of R$^d$, R$^{d'}$, R$^e$ or R$^f$ can optionally be joined to form additional rings; and $R^a$, $R^b$ and $R^c$ can optionally be joined to form additional rings;

chain

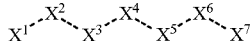

is an uninterrupted chain, wherein any bond can be a single, double or triple bond, consistent with the hybridization state of the connected atoms, e.g. if $X^2$ is an sp hybridized carbon atom and $X^3$ is also an sp hybridized carbon atom, then the $X^2$—$X^3$ bond is a triple C—C bond, etc., wherein a null selection for any of the $X^1$ to $X^7$ nodes will result in connecting the adjacent nodes, e.g. if $X^5$ is null, then $X^4$ connects to $X^6$, or if $X^4$ and $X^5$ are both null, then $X^3$ connects with $X^6$, etc., and wherein a null selection for any of the $X^1$ to $X^7$ nodes will result in an automatic null selection for the adjacent R groups, e.g. if $X^3$ is null, then $R^3$ and $R^{3'}$ are both automatically null, etc.;

$X^1$, $X^2$, $X^3$, $X^4$, $X^5$, $X^6$, and $X^7$ are each independently selected from the group consisting of null, C, CH, $CH_2$, C(=O), O, N, NH, S, S(=O) and $S(=O)_2$;

$R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$ and $R^{7'}$ are each independently selected from the group consisting of null, H, F, Cl, Br, I, CN, $NO_2$, $OR^d$, OC(=O)$R^d$, OC(=O)O$R^d$, OC(=O)N$R^dR^e$, C$R^dR^eR^f$, C$R^dR^eOR^f$, C(=O)$R^d$, C(=O)N$R^dR^e$, C(=O)O$R^d$, N$R^dR^e$, N$R^d$C(=O)$R^e$, N$R^d$C(=O)O$R^e$, N$R^d$C(=O)N$R^eR^f$, N$R^d$S(=O)$_2R^e$, N$R^d$S(=O)$_2$N$R^eR^f$, S$R^d$, S(=O)$R^d$, S(=O)$_2R^d$, and S(=O)$_2$N$R^dR^e$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^d$, OC(=O)$R^d$, OC(=O)O$R^d$, OC(=O)N$R^dR^e$, C$R^dR^eR^f$, C$R^dR^eOR^f$, C(=O)$R^d$, C(=O)N$R^dR^e$, C(=O)O$R^d$, N$R^dR^e$, N$R^d$C(=O)$R^e$, N$R^d$C(=O)O$R^e$, N$R^d$C(=O)N$R^eR^f$, N$R^d$S(=O)$_2R^e$, N$R^d$S(=O)$_2$N$R^eR^f$, S$R^d$, S(=O)$R^d$, S(=O)$_2R^d$, and S(=O)$_2$N$R^dR^e$, and wherein $R^d$, $R^{d'}$, $R^e$ and $R^f$ are each independently selected from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of $R^d$, $R^{d'}$, $R^e$ or $R^f$ can optionally be joined to form additional rings; and any of $R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$ and $R^{7'}$ can optionally be connected to each other to form various carbo- or heterocyclic systems, e.g. if $X^4$ is C, $X^5$ is CH, $X^6$ is CH, $X^7$ is C, $R^4$ is CH, $R^{4'}$ is null, $R^5$ is null, $R^{5'}$ is null, $R^6$ is null, $R^{6'}$ is null, $R^7$ is CH and $R^{7'}$ is null, then $R^4$ and $R^7$ can be connected to form a phenyl ring between $X^4$ and $X^7$; and Fn is selected from the group consisting of Formulae II, III, IV and V:

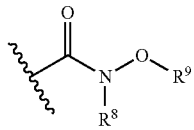

Formula II

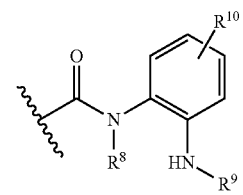

Formula III

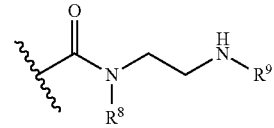

Formula IV

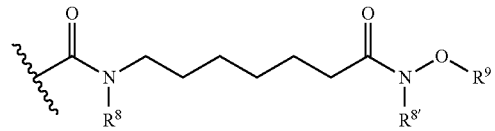

Formula V wherein in Formulae II, III, IV and V:

$R^8$, $R^{8'}$, $R^9$, and $R^{10}$ are each independently selected from the group consisting of null, H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and $R^{10}$ can represent single, multiple, or no substitution.

In one embodiment, the compound is a compound of Formula I-A. In another embodiment, the compound is a compound of Formula I-B.

In another aspect, the invention relates to a compound with a chemical structure selected from the group consisting of Formulae VI-A, VII-A, VIII-A, IX-A, X-A, VI-B, VII-B, VIII-B, IX-B, and X-B, or pharmaceutically acceptable salts thereof:

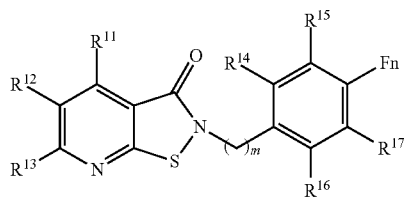

Formula VI-A

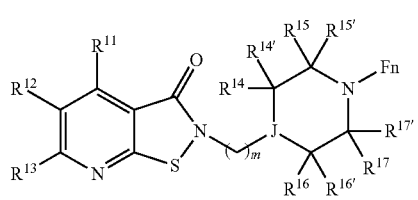

Formula VII-A

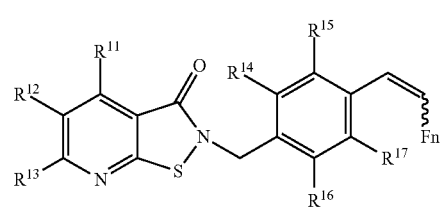

Formula VIII-A

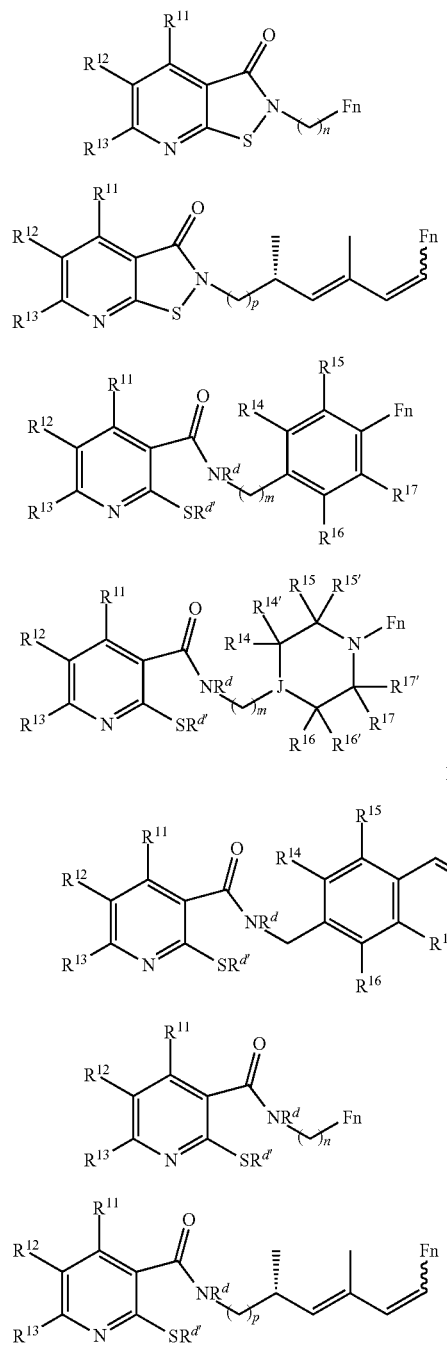
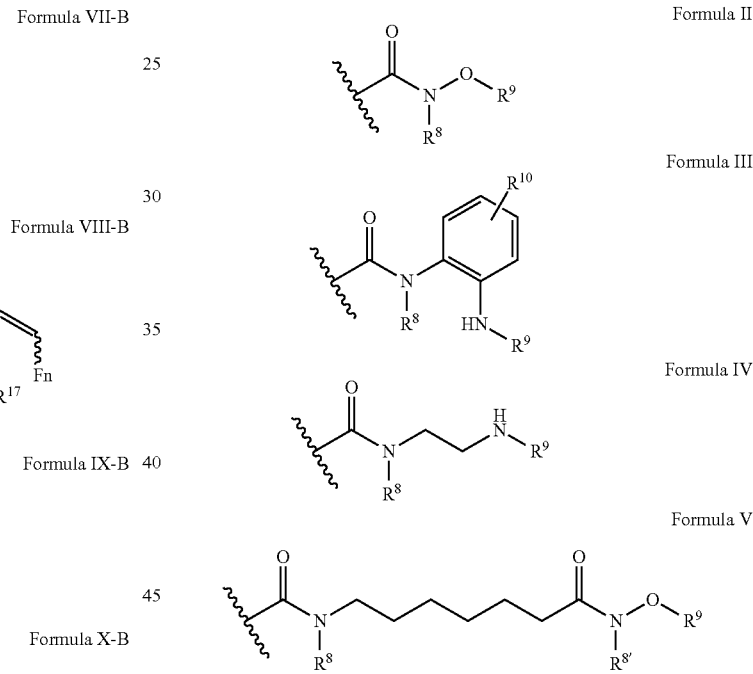

wherein in Formulae VI-A to X-B:

$R^{11}$, $R^{12}$, $R^{13}$, $R^{14}$, $R^{14'}$, $R^{15}$, $R^{15'}$, $R^{16}$, $R^{16'}$, $R^{17}$ and $R^{17'}$ are each independently selected from the group consisting of H, F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, and wherein $R^d$, $R^{d'}$, $R^e$ and $R^f$ are each independently selected from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of $R^d$, $R^{d'}$, $R^e$ or $R^f$ can optionally be joined to form additional rings; and any of $R^{11}$, $R^{12}$, $R^{13}$, $R^{14}$, $R^{14'}$, $R^{15}$, $R^{15'}$, $R^{16}$, $R^{16'}$ $R^{17}$, and $R^{17'}$ can optionally be connected to each other to form various carbo- or heterocyclic systems, e.g. if $R^{12}$ is $CH_2$ and $R^{13}$ is $OCH_2$, they can join to form a bridged tetrahydrofuran ring, etc.;

m is an integer from 0 to 3, n is an integer from 0 to 7 and p is an integer from 0 to 2;

J is selected from the group consisting of CH and N; and

Fn is selected from the group consisting of Formulae II, III, IV and V:

wherein in Formulae II, III, IV and V:

$R^8$, $R^{8'}$, $R^9$, and $R^{10}$ are each independently selected from the group consisting of null, H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and $R^{10}$ can represent single, multiple, or no substitution.

In another aspect, the invention relates to a compound having a chemical structure selected from the group consisting of RBC-1002a-A (N-(2-amino-4-(thiophen-2-yl)phenyl)-4-((3-oxoisothiazolo[5,4-b]pyridin-2(3H)-yl)methyl) benzamide), RBC-1002b-A (N-(2-amino-5-(thiophen-2-yl) phenyl)-4-((3-oxoisothiazolo[5,4-b]pyridin-2(3H)-yl) methyl)benzamide), RBC-3001-A (N-hydroxy-4-((3-oxoisothiazolo[5,4-b]pyridin-2(3H)-yl)methyl)benzamide), RBC-5001-A (N-(7-(hydroxyamino)-7-oxoheptyl)-4-((3-oxoisothiazolo[5,4-b]pyridin-2(3H)-yl)methyl)benzamide), RBC-7001-A (N-(2-aminophenyl)-4-((3-oxoisothiazolo[5,4-b]pyridin-2(3H)-yl)methyl)benzamide), RBC-1002a-B (N-(4-((2-amino-4-(thiophen-2-yl)phenyl)carbamoyl)benzyl)-2-mercaptonicotinamide), RBC-1002b-B (N-(4-((2-amino-5-(thiophen-2-yl)phenyl)carbamoyl)benzyl)-2-mercaptonicotinamide), RBC-3001-B (N-(4-(hydroxycarbamoyl)benzyl)-2-mercaptonicotinamide), RBC-5001-B (N-(4-((7-(hydroxyamino)-7-oxoheptyl)carbamoyl)benzyl)-2-mercaptonicotinamide, and RBC-7001-B (N-(4-((2-aminophenyl)carbamoyl)benzyl)-2-mercaptonicotinamide, or pharmaceutically acceptable salts thereof:

RBC-1002a-A

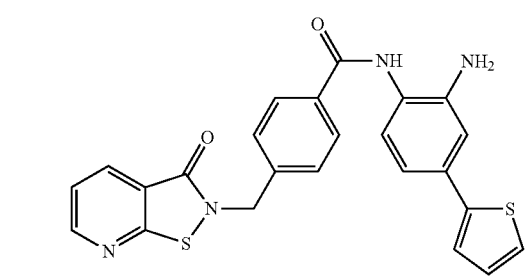

N-(2-amino-4-(thiophen-2-yl)phenyl)-
4-((3-oxoisothiazolo[5,4-b]pyridin-2
(3H)-yl)methyl)benzamide RBC-1002b-A

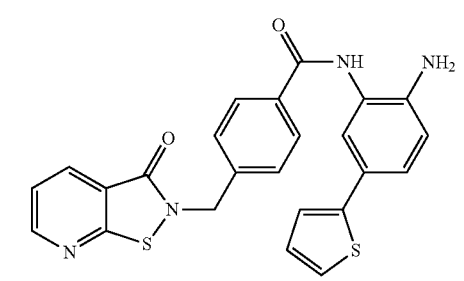

N-(2-amino-5-(thiophen-2-yl)phenyl)-
4-((3-oxoisothiazolo[5,4-b]pyridin-2
(3H)-yl)methyl)benzamide

RBC-3001-A

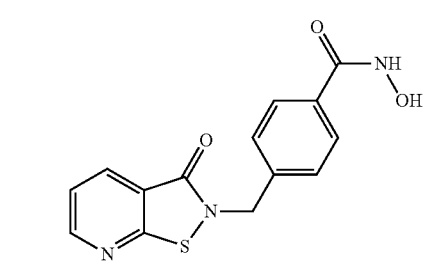

N-hydroxy-4-((3-oxoisothiazolo[5,4-b]pyridin-2
(3H)-yl)methyl)benzamide

RBC-5001-A

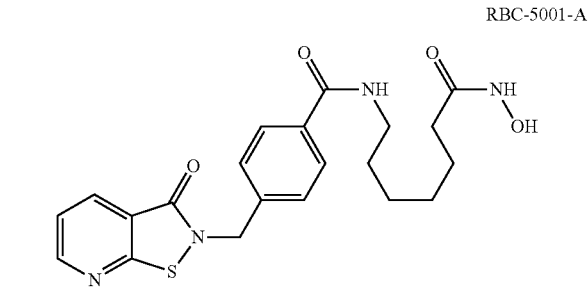

N-(7-(hydroxyamino)-7-oxoheptyl)-
4-((3-oxoisothiazolo[5,4-b]pyridin-2
(3H)-yl)methyl)benzamide

RBC-7001-A

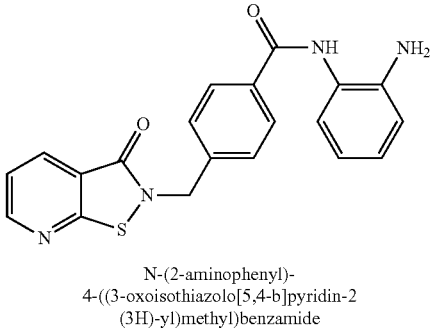

N-(2-aminophenyl)-
4-((3-oxoisothiazolo[5,4-b]pyridin-2
(3H)-yl)methyl)benzamide RBC-1002a-B

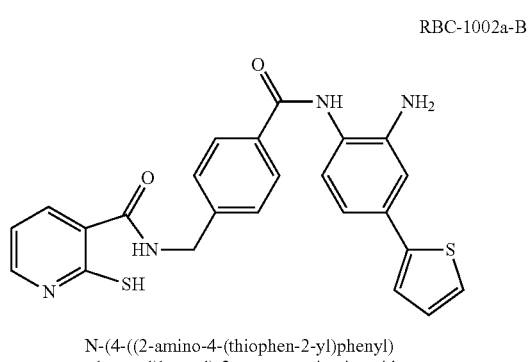

N-(4-((2-amino-4-(thiophen-2-yl)phenyl)
carbamoyl)benzyl)-2-mercaptonicotinamide RBC-1002-b-B

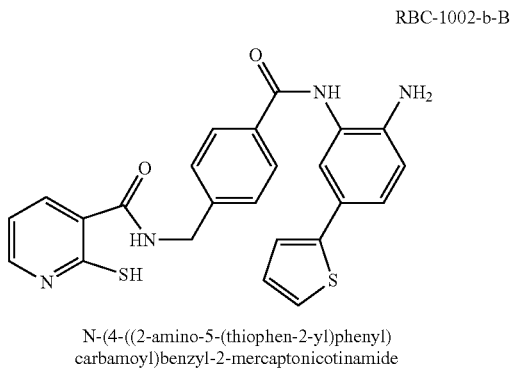

N-(4-((2-amino-5-(thiophen-2-yl)phenyl)
carbamoyl)benzyl-2-mercaptonicotinamide

RBC-3001-B

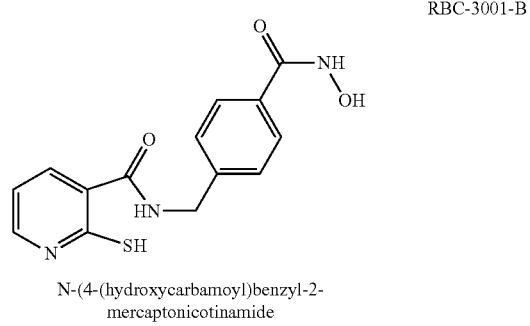

N-(4-(hydroxycarbamoyl)benzyl-2-
mercaptonicotinamide

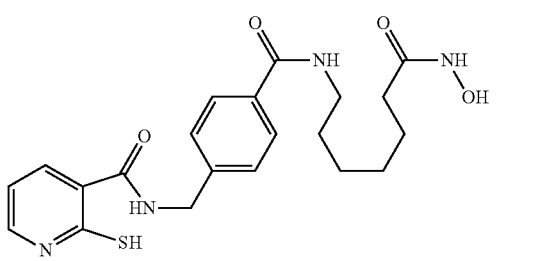

N-(4-((7-(hydroxyamino)-7-oxoheptyl)carbamoyl)benzyl)-2-mercaptonicotinamide
RBC-5001-B

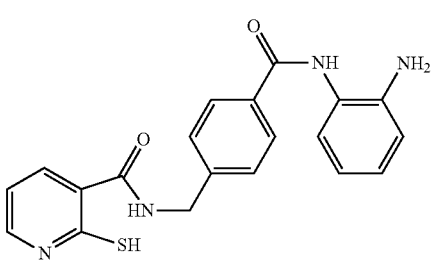

N-(4-((2-aminophenyl)carbamoyl)benzyl)-2-mercaptonicotinamide
RBC-7001-B

Synthesis of the Compounds of the Invention

The compounds of the invention can be prepared by a person skilled in the art of synthetic organic chemistry once armed with the teachings herein. The person skilled in the art knows how to select and implement appropriate synthetic routes. Suitable synthetic methods may be identified by reference to the literature describing synthesis of analogous compounds, and then performing the synthesis of the desired compound following the route used for the analogous compounds, modifying the starting materials, reagents, and reaction conditions as appropriate to synthesizing any particular desired compounds. In addition, reference may be made to sources such as Comprehensive Organic Synthesis, Ed. B. M. Trost and I. Fleming (Pergamon Press 1991), Comprehensive Organic Functional Group Transformations, Ed. A. R. Katritzky, O. Meth Cohn, and C. W. Rees (Pergamon Press, 1996), Comprehensive Organic Functional Group Transformations II, Ed. A. R. Katritzky and R. J. K. Taylor (Editor) (Elsevier, 2nd Edition, 2004), Comprehensive Heterocyclic Chemistry, Ed. A. R. Katritzky and C. W. Rees (Pergamon Press, 1984), and Comprehensive Heterocyclic Chemistry II, Ed. A. R. Katritzky, C. W. Rees, and E. F. V. Scriven (Pergamon Press, 1996), the entire disclosures of which are incorporated herein by reference. In one embodiment of the invention, the starting materials and intermediates required for the synthesis may be obtained from commercial sources or synthesized according to methods known to those skilled in the art. In various embodiments, a compound of the invention can be synthesized according to Scheme 1, Scheme 2, Scheme 3, Scheme 4, or any variations thereof apparent to one skilled in the art.

Scheme 1

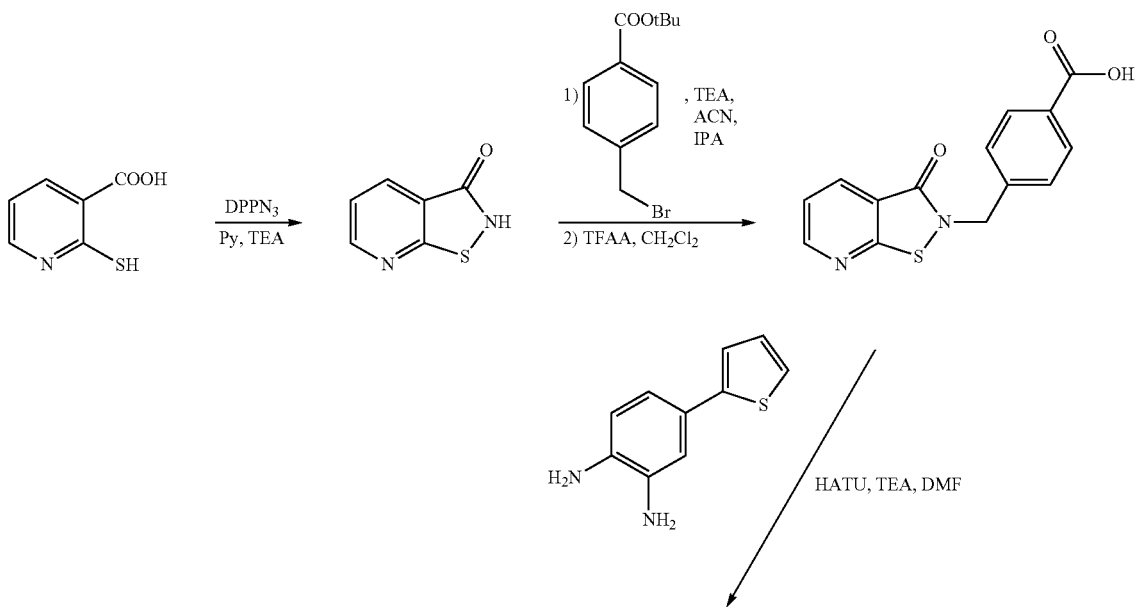

29

RBC-1002a-A

30

RBC-1002b-A

Scheme 2

1) NH$_2$O-THP
EDAC, HOPt
N-methyl-morpholine
2) Si-TSOH (SCX-3)

RBC-3001-A

RBC-5001-A

1) NH$_2$O-THP
EDAC, HOPt
N-methyl-morpholine
2) Si-TsOH (SCX-3)

Scheme 3

1) NH$_2$(CH$_2$)$_6$COOtBu
EDAC, HOPt
N-methyl-morpholine
2) TFAA, CH$_2$Cl$_2$ Scheme 4

EDAC, HOPt
N-methyl-morpholine

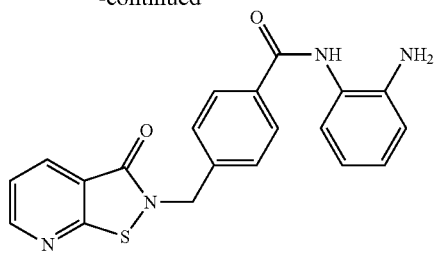

RBC-7001-A

It will be understood that when compounds of the invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention that are efficacious in inhibiting HDACs. The isomers resulting from the presence of a chiral center comprise a pair of non-superimposable isomers that are called "enantiomers." Single enantiomers of a pure compound are optically active, i.e., they are capable of rotating the plane of plane polarized light. Enantiomers may be purified from racemic mixtures by well-known chiral separation techniques. According to one such method, a racemic mixture of a compound having the structure of Formula I or a chiral intermediate thereof, is separated into 99% wt % pure optical isomers by HPLC using a suitable chiral column, such as a member of the series of DAICEL® CHIRALPAK® family of columns (Daicel Chemical Industries, Ltd., Tokyo, Japan), operated according to the manufacturer's instructions. By "isolated optical isomer" it is understood a compound that has been substantially purified from the corresponding optical isomer(s) of the same formula. In some embodiments, the isolated isomer is at least about 80% pure by weight. In some embodiments, the isolated isomer is at least about 90% pure by weight. In some embodiments, the isolated isomer is at least about 98% pure by weight. In some embodiments, the isolated isomer is at least about 99% pure, by weight. Diastereoisomeric pairs may be resolved by known separation techniques including normal and reverse phase chromatography, and crystallization.

Metabolites, N-Oxides, and Other Analogs

The compounds, methods, and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, sites on, for example, the isothiazole ring portion of compounds of series "A" of the invention are susceptible to various metabolically driven transformations after administration to a subject, for example cleavage of the S—N bond. In one embodiment, metabolically driven transformations can transform a substituted isothiazolo pyridin-one of the invention (a series "A" compound) into a substituted 2-mercaptonicotinamide of the invention (a series "B" compound). In other embodiments, the substituted isothiazolo pyridin-ones of the invention (series "A" compounds), and the substituted 2-mercaptonicotinamides of the invention (series "B" compounds), can both be synthesized de novo.

Series "A" Compounds          Series "B" Compounds

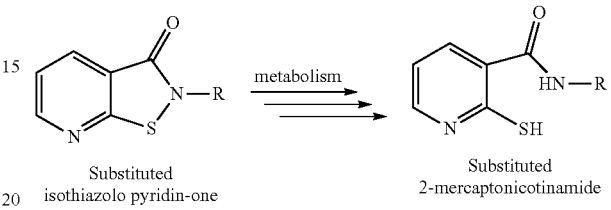

Substituted isothiazolo pyridin-one      Substituted 2-mercaptonicotinamide

If necessary, incorporation of appropriate substituents on the series "A" compounds may reduce, minimize or eliminate this or other metabolic pathway, as would be understood by one of ordinary skill in the art. In one embodiment, the appropriate substituent to decrease or eliminate the susceptibility of metabolic reactions is, by way of example only, a deuterium, a halogen, or an alkyl group.

In one aspect, the invention is directed to metabolites of series "A" compounds, particularly human metabolites. Thus, the metabolites may be referred to hereinafter as "human metabolites." Human metabolites of series "A" compounds include metabolites of series "A" compounds, for example series "B" compounds that are formed in the bodies of human subjects after ingestion or application of series "A" compounds according to clinical protocols regarding dosing and monitoring, including those described herein. In various embodiments, the term encompasses molecular species formed in vivo, whether or not the species is even detected or analyzed in a particular trial. It is also contemplated that some metabolites are unique to particular individuals, reflecting different genetic make-up and the presence and activity of various enzymes, including cytochrome P450 and UGT enzymes, which are involved in metabolism. Thus, human metabolites cover all such metabolites formed in the human body, including but not limited to series "B" compounds.

In various embodiments, the series "A" compounds metabolites, including series "B" compounds, are isolated from body tissues and fluids, and/or are prepared synthetically according to methods available to the skilled artisan. A variety of separation processes can be carried out on tissue and fluid samples to provide samples for further analysis, such as nuclear magnetic resonance, gas chromatography (GC), liquid chromatography (LC), and mass spectrometry. In such samples, the metabolites are contained in compositions that are essentially lacking in the presence of any of the other metabolites. The presence of the metabolites can be quantified by physical methods, such as the measurement of nuclear decay from radioactive isotopes, measurement of index of refraction, flame ionization, ionization and deflection in magnetic fields, ultraviolet (UV absorption), and the like.

Formulations, Prodrugs, and Salts

In one embodiment, the invention provides use of the compounds of the invention for the manufacture and preparation of medicaments for use in therapy. In another embodiment, an effective inhibitor of HDACs retains its activity when mixed with an acceptable pharmaceutical carrier. In another embodiment, the invention further provides novel compounds and novel pharmaceutical compositions comprising the same and at least one pharmaceutically acceptable carrier.

The invention includes prodrugs of the compounds of the invention. "Prodrug," as used herein, means a compound which is convertible in vivo by metabolic means (e.g., by hydrolysis) to a compound of the present invention. Various forms of prodrugs are known in the art, for example, as discussed in Bundgaard, (ed.), Design of Prodrugs, Elsevier (1985); Widder et al. (ed.), Methods in Enzymology, vol. 4, Academic Press (1985); Krogsgaard-Larsen et al. (ed). "Design and Application of Prodrugs," Textbook of Drug Design and Development, Chapter 5, 113-191 (1991), Bundgaard et al., 1992, J. Drug Deliv. Rev. 8:1-38, Bundgaard, 1988, J. Pharm. Sci. 77:285 et seq.; and Higuchi and Stella (eds.), Prodrugs as Novel Drug Delivery Systems, American Chemical Society (1975). In one non-limiting example, the esters and amides of the alpha-carboxylic acid are prepared as prodrugs to improve oral bioavailability, whereby the ester or amide is stable in the stomach and gastrointestinal tract, is optimally transported across the lining of the gastrointestinal tract into the bloodstream, and is then converted by the ubiquitous esterases or amidases in the blood to the carboxylic acid moiety. In another non-limiting example, the ester prodrug is the methyl, ethyl, n-propyl or i-propyl ester. In another non-limiting example, the amide prodrug is the isopropyl amide or the 2,2,2-trifluoroethyl amide.

The compounds useful in the invention may form salts with acids or bases, and such salts are included in the present invention. In one embodiment, the salts are pharmaceutically-acceptable salts. The term "salts" embraces addition salts of free acids or free bases that are compounds useful within the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, O-hydroxybutyric, salicylic, galactaric and galacturonic acid.

Suitable pharmaceutically acceptable base addition salts of compounds useful in the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared from the corresponding compound by reacting, for example, the appropriate acid or base with the compound.

Methods of the Invention

The invention includes methods for inhibiting HDACs, and methods for treating in a subject a disease or disorder associated with HDACs. In one embodiment, the subject is a human. In one embodiment, the invention includes a method of preventing or treating a disease or disorder, comprising administering a compound of the invention to a subject in need of such prevention or treatment, wherein the amount of the compound is sufficient for the prevention or treatment of the disease or disorder in the subject.

In one embodiment, the method comprises administering to the subject a therapeutically effective amount of a compound of Formula I-A, and/or Formula I-B, or salts or solvates thereof:

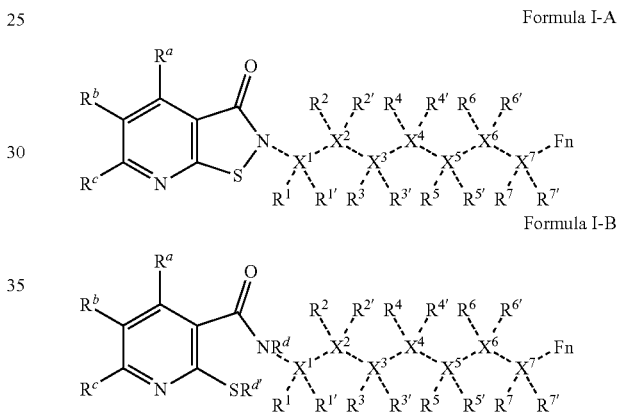

Formula I-A

Formula I-B wherein in Formulae I-A and I-B:

$R^a$, $R^b$ and $R^c$ are each independently selected from the group consisting of H, F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, and wherein $R^d$, $R^{d'}$, $R^e$ and $R^f$ are each independently selected from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of $R^d$, $R^{d'}$, $R^e$ or $R^f$ can optionally be joined to form additional rings; and $R^a$, $R^b$ and $R^c$ can optionally be joined to form additional rings;

chain

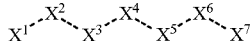

is an uninterrupted chain, wherein any bond can be a single, double or triple bond, consistent with the hybridization state of the connected atoms, e.g. if $X^2$ is an sp hybridized carbon atom and $X^3$ is also an sp hybridized carbon atom, then the $X^2$—$X^3$ bond is a triple C—C bond, etc., wherein a null selection for any of the $X^1$ to $X^7$ nodes will result in connecting the adjacent nodes, e.g. if $X^5$ is null, then $X^4$ connects to $X^6$, or if $X^4$ and $X^5$ are both null, then $X^3$ connects with $X^6$, etc., and wherein a null selection for any of the $X^1$ to $X^7$ nodes will result in an automatic null selection for the adjacent R groups, e.g. if $X^3$ is null, then $R^3$ and $R^{3'}$ are both automatically null, etc.;

$X^1$, $X^2$, $X^3$, $X^4$, $X^5$, $X^6$, and $X^7$ are each independently selected from the group consisting of null, C, CH, $CH_2$, C(=O), O, N, NH, S, S(=O) and $S(=O)_2$;

$R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$ and $R^{7'}$ are each independently selected from the group consisting of null, H, F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, and wherein $R^d$, $R^{d'}$, $R^e$ and $R^f$ are each independently selected from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of $R^d$, $R^{d'}$, $R^e$ or $R^f$ can optionally be joined to form additional rings; and any of $R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^1$ and $R^{7'}$ can optionally be connected to each other to form various carbo- or heterocyclic systems, e.g. if $X^4$ is C, $X^5$ is CH, $X^6$ is CH, $X^7$ is C, $R^4$ is CH, $R^{4'}$ is null, $R^5$ is null, $R^{5'}$ is null, $R^6$ is null, $R^{6'}$ is null, $R^7$ is CH and $R^{7'}$ is null, then $R^4$ and $R^7$ can be connected to form a phenyl ring between $X^4$ and $X^7$; and Fn is selected from the group consisting of Formulae II, III, IV and V:

Formula II

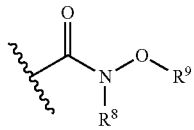

Formula III

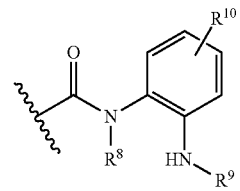

Formula IV

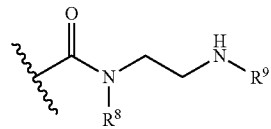

Formula V

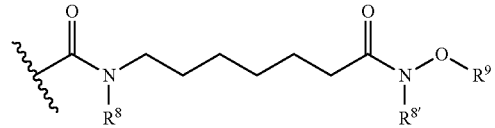

wherein in Formulae II, III, IV and V:

$R^8$, $R^{8'}$, $R^9$, and $R^{10}$ are each independently selected from the group consisting of null, H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and $R^{10}$ can represent single, multiple, or no substitution.

In another embodiment, the method comprises administering to the subject a therapeutically effective amount of a compound selected from the group consisting of Formulae VI-A, VII-A, VIII-A, IX-A, X-A, VI-B, VII-B, VIII-B, IX-B, and X-B, or pharmaceutically acceptable salts thereof:

Formula VI-A

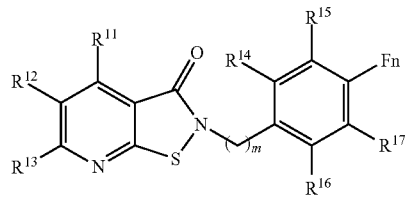

Formula VII-A

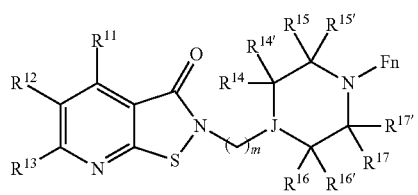

Formula VIII-A

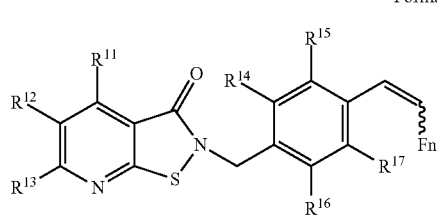

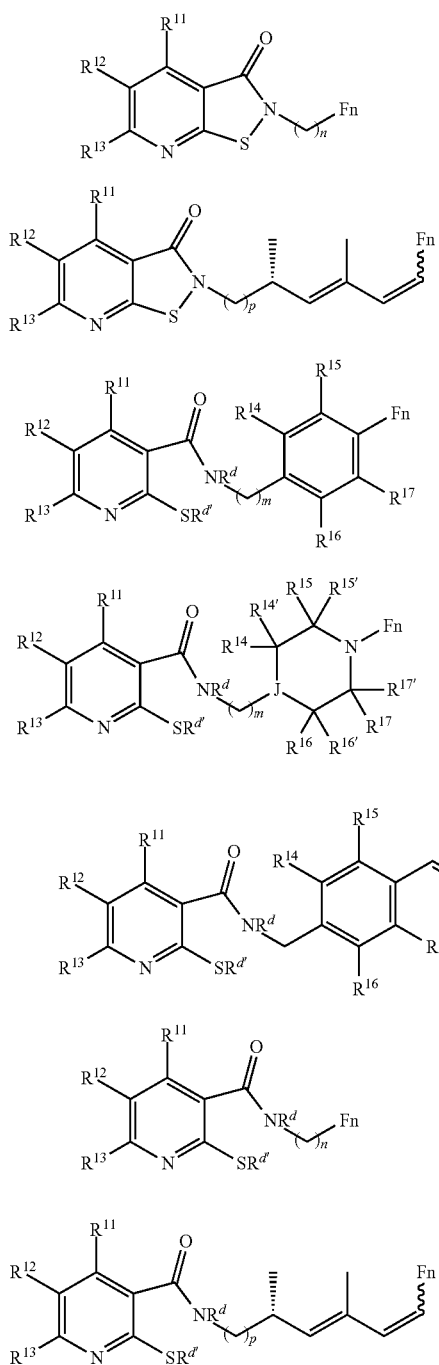

Formula IX-A

Formula X-A

Formula VI-B

Formula VII-B

Formula VIII-B

Formula IX-B

Formula X-B wherein in Formulae VI-A to X-B:
$R^{11}$, $R^{12}$, $R^{13}$, $R^{14}$, $R^{14'}$, $R^{15}$, $R^{15'}$, $R^{16}$, $R^{16'}$, $R^{17}$ and $R^{17'}$ are each independently selected from the group consisting of H, F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, and wherein $R^d$, $R^{d'}$, $R^e$ and $R^f$ are each independently selected from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of $R^d$, $R^{d'}$, $R^e$ or $R^f$ can optionally be joined to form additional rings; and any of $R^{11}$, $R^{12}$, $R^{13}$, $R^{14}$, $R^{14'}$, $R^{15}$, $R^{15'}$, $R^{16}$, $R^{16'}$ $R^{17}$ and $R^{17'}$ can optionally be connected to each other to form various carbo- or heterocyclic systems, e.g. if $R^{12}$ is $CH_2$ and $R^{13}$ is $OCH_2$, they can join to form a bridged tetrahydrofuran ring, etc.;

m is an integer from 0 to 3, n is an integer from 0 to 7 and p is an integer from 0 to 2;

J is selected from the group consisting of CH and N; and

Fn is selected from the group consisting of Formulae II, III, IV and V:

Formula II

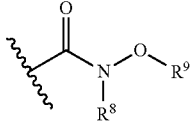

Formula III

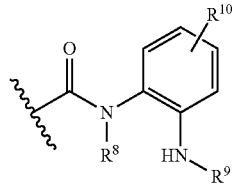

Formula IV

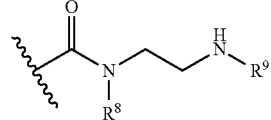

Formula V

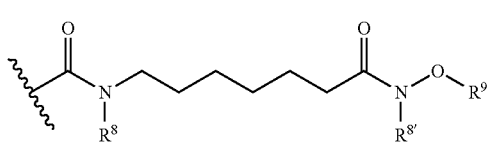

wherein in Formulae II, III, IV and V:
$R^8$, $R^{8'}$, $R^9$, and $R^{10}$ are each independently selected from the group consisting of null, H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and $R^{10}$ can represent single, multiple, or no substitution.

In another embodiment, the method of treatment comprises administering to the subject a therapeutically effective amount of a compound having a chemical structure selected from the group consisting of RBC-1002a-A (N-(2-amino-4-(thiophen-2-yl)phenyl)-4-((3-oxoisothiazolo[5,4-b]pyridin-2(3H)-yl)methyl)benzamide), RBC-1002b-A (N-(2-amino- 5-(thiophen-2-yl)phenyl)-4-((3-oxoisothiazolo[5,4-b]pyridin-2(3H)-yl)methyl)benzamide), RBC-3001-A (N-hydroxy-4-((3-oxoisothiazolo[5,4-b]pyridin-2(3H)-yl)methyl)benzamide), RBC-5001-A (N-(7-(hydroxyamino)-7-oxoheptyl)-4-((3-oxoisothiazolo[5,4-b]pyridin-2(3H)-yl)methyl)benzamide), RBC-7001-A (N-(2-aminophenyl)-4-((3-oxoisothiazolo[5,4-b]pyridin-2(3H)-yl)methyl)benzamide), RBC-1002a-B (N-(4-((2-amino-4-(thiophen-2-yl)phenyl)carbamoyl)benzyl)-2-mercaptonicotinamide), RBC-1002b-B (N-(4-((2-amino-5-(thiophen-2-yl)phenyl)carbamoyl)benzyl)-2-mercaptonicotinamide), RBC-3001-B (N-(4-(hydroxycarbamoyl)benzyl)-2-mercaptonicotinamide), RBC-5001-B (N-(4-((7-(hydroxyamino)-7-oxoheptyl)carbamoyl)benzyl-2-mercaptonicotinamide, and RBC-7001-B (N-(4-((2-aminophenyl)carbamoyl)benzyl)-2-mercaptonicotinamide, or pharmaceutically acceptable salts thereof:

RBC-1002a-A

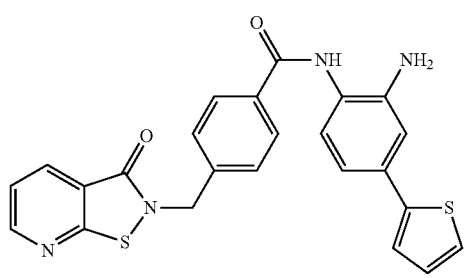

N-(2-amino-4-(thiophen-2-yl)phenyl)-
4-((3-oxoisothiazolo[5,4-b]pyridin-2
(3H)-yl)methyl)benzamide RBC-1002b-A

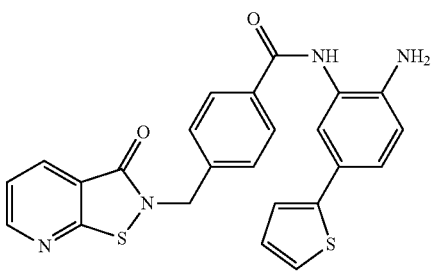

N-(2-amino-5-(thiophen-2-yl)phenyl)-
4-((3-oxoisothiazolo[5,4-b]pyridin-2
(3H)-yl)methyl)benzamide

RBC-3001-A

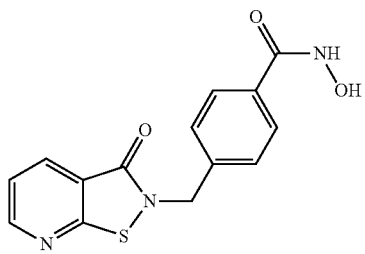

N-hydroxy-4-((3-oxoisothiazolo[5,4-b]pyridin-2
(3H)-yl)methyl)benzamide

-continued

RBC-5001-A

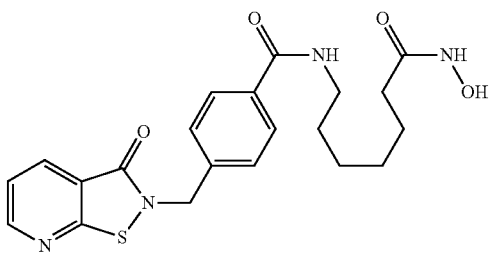

N-(7-(hydroxyamino)-7-oxoheptyl)-
4-((3-oxoisothiazolo[5,4-b]pyridin-2
(3H)-yl)methyl)benzamide

RBC-7001-A

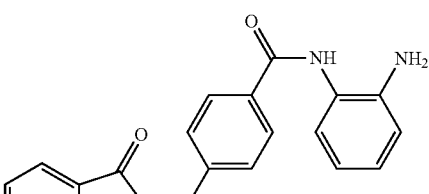

N-(2-aminophenyl)-
4-((3-oxoisothiazolo[5,4-b]pyridin-2
(3H)-yl)methyl)benzamide RBC-1002a-B

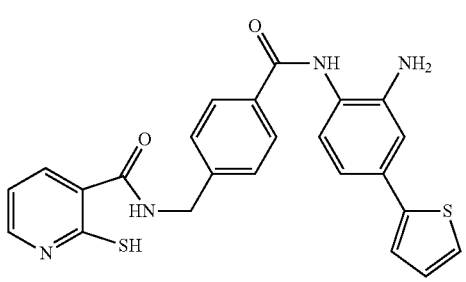

N-(4-((2-amino-4-(thiophen-2-yl)phenyl)
carbamoyl)benzyl)-2-mercaptonicotinamide RBC-1002-b-B

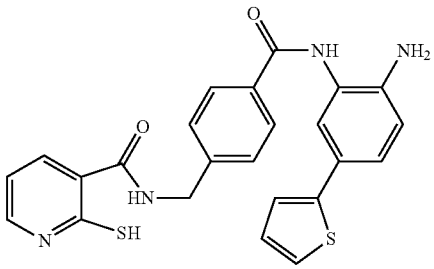

N-(4-((2-amino-5-(thiophen-2-yl)phenyl)
carbamoyl)benzyl-2-mercaptonicotinamide

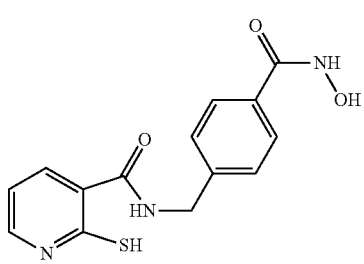

RBC-3001-B

N-(4-(hydroxycarbamoyl)benzyl-2-mercaptonicotinamide

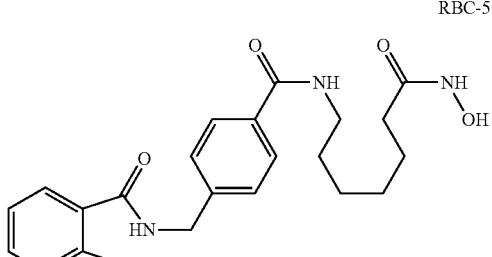

RBC-5001-B

N-(4-((7-(hydroxyamino)-7-oxoheptyl)carbamoyl)benzyl)-2-mercaptonicotinamide

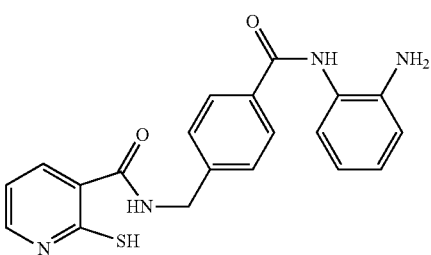

RBC-7001-B

N-(4-((2-aminophenyl)carbamoyl)benzyl)-2-mercaptonicotinamide

In one aspect, the invention relates to a method of inhibiting HDAC. In one embodiment, the compound of the invention inhibits several HDACs. In another embodiment, the compound of the invention inhibits at least one HDAC. In another embodiment, the compound of the invention inhibits only a small group of HDACs. In another embodiment, the compound of the invention inhibits only one class of HDACs. In one embodiment, the compound of the invention selectively inhibits class I HDACs. In another embodiment, the compound of the invention selectively inhibits class IIA HDACs. In another embodiment, the compound of the invention selectively inhibits class IIB HDACs. In another embodiment, the compound of the invention selectively inhibits class III HDACs. In yet another embodiment, the compound of the invention selectively inhibits class IV HDACs.

In one embodiment, the compound of the invention selectively inhibits only part of a class of HDACs. In one embodiment, the compound of the invention inhibits only one HDAC. In another embodiment, the compound of the invention selectively inhibits HDAC1. In another embodiment, the compound of the invention selectively inhibits HDAC2. In another embodiment, the compound of the invention selectively inhibits HDAC3. In another embodiment, the compound of the invention selectively inhibits HDAC4. In another embodiment, the compound of the invention selectively inhibits HDAC5. In another embodiment, the compound of the invention selectively inhibits HDAC6. In another embodiment, the compound of the invention selectively inhibits HDAC7. In another embodiment, the compound of the invention selectively inhibits HDAC8. In another embodiment, the compound of the invention selectively inhibits HDAC9. In another embodiment, the compound of the invention selectively inhibits HDAC10. In another embodiment, the compound of the invention selectively inhibits HDAC11. In another embodiment, the compound of the invention selectively inhibits SIRT1. In another embodiment, the compound of the invention selectively inhibits SIRT2. In another embodiment, the compound of the invention selectively inhibits SIRT3. In another embodiment, the compound of the invention selectively inhibits SIRT4. In another embodiment, the compound of the invention selectively inhibits SIRT5. In another embodiment, the compound of the invention selectively inhibits SIRT6. In another embodiment, the compound of the invention selectively inhibits SIRT7.

In another embodiment, the invention provides a method of treating HDAC-associated diseases and disorders. In one embodiment, the method includes administering to a patient a therapeutically effective amount of a compound of the invention. In one embodiment, the invention provides a method of treating a disease or disorder related to the enzymatic control of the acetylation state of protein lysine residues, more specifically those contained in the N-terminal extensions of the core histones. In one embodiment, invention provides a method of treating a disease or disorder associated with the overexpression of one or more HDACs. In one embodiment, the disease or disorder is cancer, such as, but not limited to, multiple myeloma, leukemia, lymphoma, breast cancer, lung cancer, stomach cancer, liver cancer, blood cancer, bone cancer, pancreatic cancer, skin cancer, head or neck cancer, skin or eye melanoma, sarcoma of the uterus, ovarian cancer, rectal cancer, anal cancer, colorectal cancer, fallopian tube carcinoma, endometrium carcinoma, cervical cancer, small intestine cancer, endocrine gland cancer, thyroid cancer, parathyroid gland cancer, renal cell carcinoma, soft tissue sarcoma, urethra cancer, prostate cancer, bronchial cancer, myeloma, neuroma, cutaneous squamous cell carcinoma, or the like.

In another aspect, the invention provides a method of treating a neurological disease or disorder. In another embodiment, the invention provides a method of treating an inflammatory disease or disorder. In other various embodiments, the diseases and disorders include, but are not limited to, diseases and disorders related to cell migration, cell spreading, immune synapse formation, viral infection, the degradation of misfolded proteins and stress granule (SG) formation. In yet another embodiment, the disease or disorder is Alzheimer's disease. In yet another embodiment, the disease or disorder is an autoimmune disease or disorder. In other various embodiments, the diseases and disorders treatable by the compound of the invention include, but are not limited to, diseases and disorders related to neurological disease, a neurodegenerative disorder, a neurodegenerative disease, neuroinflammation, pain, epilepsy, stroke, traumatic brain injury, allograft rejection, or a parasite related disease. In one embodiment, the neuroinflammation disease or disorder is the Charcot-Marie-Tooth (CMT) disease. In other embodiments, a disease or disorder is Huntington's disease, Parkinson's disease, ischemic stroke, amyotrophic lateral sclerosis (ALS) and spinal muscular atrophy, pain, anxiety and depression, bone and muscle-related disorders such as cancer-induced cachexia, Gaucher's disease, and neuroblastoma.

In another embodiment, the disease or disorder is a pathological autoimmune disorder such as juvenile oligoarthritis, collagen-induced arthritis, adjuvant-induced arthritis, Sjogren's syndrome, multiple sclerosis, experimental autoimmune encephalomyelitis, inflammatory bowel disease (for example, Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia, pernicious anemia, and the like.

In another aspect, the invention provides a method of immunomodulation for organ transplant. In one embodiment, the method includes administering to a patient a therapeutically effective amount of a compound of the invention. In one embodiment, the method confers improved or superior retention of organ transplants.

In one embodiment of the method of the invention, the compound of the invention is administered in combination with a second therapeutic agent for the treatment of a disease or disorder. In another embodiment, the second therapeutic agent is administered simultaneously, prior to, or after administration of the compound of the invention. In yet another embodiment, the second therapeutic agent is co-administered with the compound of the invention. In yet another embodiment, the second therapeutic agent is co-administered and co-formulated with the compound of the invention. In one embodiment, the second therapeutic agent is a DNA-damaging chemotherapeutics such as idarubicin and cytarabine for the treatment of AML and MDS. In another embodiment, the second therapeutic agent is a proteasome inhibitor such as bortezomib for the treatment of relapsing and/or refractory multiple myeloma and lymphoma. In another embodiment, the second therapeutic agent is an anti-androgen receptor agent such as bicalutamide for the treatment of prostate cancer.

In some embodiments, one or more additional pharmaceutical agents can be used, such as, for example, immunomodulatory or immunotherapeutic drugs, such as immune checkpoint inhibitor monoclonal antibodies, thalidomide, lenalidomide (Len) and pomalidomide, steroids, such as dexamethasone, anticancer antibodies, such as nivolumab and ipilimumab, proteasome inhibitors, such as bortezomib, salinosporamide, anticancer drugs, such as romidepsin, and taxanes, oncolytic viral therapy agents, such as adenovirus, reovirus, or herpes simplex.

In one embodiment, the second therapeutic agent is a DNA-damaging chemotherapeutics such as idarubicin and cytarabine for the treatment of AML and MDS. In another embodiment, the second therapeutic agent is a proteasome inhibitor such as bortezomib for the treatment of relapsing and/or refractory multiple myeloma and lymphoma. In another embodiment, the second therapeutic agent is an antiandrogen receptor agent such as bicalutamide for the treatment of prostate cancer.

In some embodiments, the second therapeutic agent is an antiretroviral drug. In other embodiments, the second therapeutic agent is a reverse-transcriptase inhibitor. In other embodiments, the second therapeutic agent can be lamivudine, zidovudine, lopinavir, ritonavir, abacavir, tenofovir, emtricitabine, rilpivirine, efavirenz, elvitegravir, cobicistat, dolutegravir, darunavir, atazanavir, and raltegravir.

In certain embodiments, the compound of the invention may be administered to a subject in conjunction with (e.g., before, simultaneously, or following) any number of relevant treatment modalities including chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludarabine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the compounds of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the compounds of the present invention are administered following B-cell ablative therapy such as agents that react with CD20, e.g., Rituxan.

Without wishing to be bound by any particular theory, it is believed that the ability of the compounds of the invention to regulate the biological activity of HDACs provides methods of treating HDACs related disorders. For example, the compounds of the invention can be used to suppress HDACs activity, whether HDACs are overexpressed or not.

Dosing

The compounds of the invention, alone or in combination with another therapeutic agent, can be administered to a cell, a tissue, or a subject to provide a therapeutic effect. Methods for the safe and effective administration of the compounds of the invention are known to those skilled in the art. For instance, the administration of HDACs inhibitors is described in the literature.

Dosages of the compounds of the invention range from about 0.1 µg/day to 10,000 mg/day, from about 1 µg/day to 1000 mg/day, and from about 10 µg/day to 100 mg/day, and any and all whole or partial increments there between.

Stated in terms of subject body weight, dosages range from about 0.1 µg/kg/day to about 1000 mg/kg/day, from about 10 µg/kg/day to about 500 mg/kg/day, from about 20 µg/kg/day to about 100 mg/kg/day, from about 50 µg/kg/day to about 50 mg/kg/day, and from about 0.10 mg/kg/day to about 5 mg/kg/day, and any and all whole or partial increments there between.

Oral dosages of the compounds of the invention range from about 0.1 µg/day to about 10,000 mg/day, from about 1 µg/day to about 1000 mg/day, from about 10 µg/day to about 100 mg/day, and from about 8 mg/day to about 80 mg/day, and any and all whole or partial increments there between.

Stated in terms of subject body weight, oral dosages range from about 0.1 µg/kg/day to about 1000 mg/kg/day, from about 10 µg/kg/day to about 500 mg/kg/day, from about 20 µg/kg/day to about 100 mg/kg/day, from about 50 µg/kg/day to about 50 mg/kg/day, and from about 0.10 mg/kg/day to about 5 mg/kg/day, and any and all whole or partial increments there between.

The compounds of the invention for administration can be administered in a dose range of from about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, and any and all whole or partial increments there between.

In some embodiments, the dose of the compound of the invention is from about 0.0001 mg to about 25 mg. In some embodiments, a dose of a compound of the invention used in compositions described herein is less than about 100 mg, or less than about 80 mg, or less than about 60 mg, or less than about 50 mg, or less than about 30 mg, or less than about 20 mg, or less than about 10 mg, or less than about 5 mg, or less than about 2 mg, or less than about 0.5 mg. Similarly, in some embodiments, a dose of a second compound as described herein is less than about 1000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments there between.

Pharmaceutical Composition

For administration of a compound of the present invention to a subject, the compound can be suspended in any pharmaceutically acceptable carrier, for example, sterile water or buffered aqueous carriers, such as glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey), the disclosure of which is incorporated by reference as if set forth in its entirety herein.

The pharmaceutical compositions comprising a compound of the invention may be prepared, packaged, or sold in the form of a sterile injectable aqueous or oily suspension or solution. This suspension or solution may be formulated according to the known art, and may comprise, in addition to the active ingredient, additional ingredients such as dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

The compositions of the invention are preferably administered to the subject as a pharmaceutical or veterinary composition, which includes systemic and topical formulations. Among these, preferred are formulations suitable for inhalation, or for respirable, buccal, oral, rectal, vaginal, nasal, intrapulmonary, ophthalmic, optical, intracavitary, intratracheal, intraorgan, topical (including buccal, sublingual, dermal and intraocular), parenteral (including subcutaneous, intradermal, intramuscular, intravenous and intraarticular) and transdermal administration, among others. The route(s) of administration will be readily apparent to the skilled artisan and will depend upon any number of factors including the type and severity of the disease being treated, the type and age of the veterinary or human patient being treated.

The compositions of the invention may be administered to the lungs of a subject by any suitable means, but are preferably administered by generating an aerosol or spray comprised of respirable, inhalable, nasal or intrapulmonarily delivered particles comprising the active compound, which particles the subject inhales, i.e., by inhalation administration. The respirable particles may be liquid or solid. Particles comprising the active compound for practicing the present invention should include particles of respirable or inhalable size; that is, particles of a size sufficiently small to pass through the mouth and larynx upon inhalation and into the bronchi and alveoli of the lungs. In general, particles ranging from about 0.05, about 0.1, about 0.5, about 1, about 1.5 to about 5, about 6, about 7, about 8, about 10 microns in size, more particularly particles about 0.5 to less than about 5 microns in size, are respirable or inhalable. When particles of nonrespirable size are included in the aerosol or spray, they tend to deposit in the throat and be swallowed. Thus, the quantity of non-respirable particles in the aerosol or spray is preferably minimized when intended for respirable administration or by inhalation. For nasal or intrapulmonary administration, a particle size in the range of about 10, about 11, about 15, about 20 to about 25, about 30, about 40, about 50, and sometimes even up to about 100 and about 500 microns is preferred to ensure retention in the nasal or pulmonary cavity. Pulmonary instillation is particularly useful in treating newborns.

Liquid pharmaceutical compositions of the compound of the invention for producing an aerosol or spray may be prepared by combining the active compound with a stable vehicle, such as sterile pyrogen free water. Solid particulate compositions containing respirable dry particles of micronized active compound may be prepared by grinding dry active compound with a mortar and pestle, and then passing the micronized composition through a 400 mesh screen to break up or separate out large agglomerates. A solid particulate composition comprised of the active compound may optionally contain a dispersant which serves to facilitate the formation of an aerosol. A suitable dispersant is lactose, which may be blended with the active compound in any suitable ratio, e.g., a 1 to 1 ratio by weight. Other therapeutic and formulation compounds may also be included, such as a surfactant to improve the state of surfactant in the lung and to help with the absorption of the active agent.

Aerosols of liquid particles comprising the active compound may be produced by any suitable means, such as with a nebulizer. See, e.g., U.S. Pat. No. 4,501,729. Nebulizers are commercially available devices which transform solutions or suspensions of the active ingredient into a therapeutic aerosol mist either by means of acceleration of a compressed gas, typically air or oxygen, through a narrow venturi orifice or by means of ultrasonic agitation. Suitable compositions for use in nebulizer consist of the active ingredient in liquid carrier, the active ingredient comprising up to 40% w/w of the compositions, but preferably less than 20% w/w, and the carrier is typically water or a dilute aqueous alcoholic solution, preferably made isotonic with body fluids by the addition of, for example sodium chloride. Optional additives include preservatives if the composition is not prepared sterile, for example, methyl hydroxybenzoate, antioxidants, flavoring agents, volatile oils, buffering agents and surfactants.

Aerosols of solid particles comprising the active compound may likewise be produced with any sold particulate medicament aerosol generator. Aerosol generators for administering solid particulate medicaments to a subject produce particles which are respirable, as explained above, and they generate a volume of aerosol containing a predetermined metered dose of a medicament at a rate suitable for human administration. Examples of such aerosol generators include metered dose inhalers and insufflators.

Pharmaceutical compositions that are useful in the methods of the invention may be administered systemically in oral solid formulations, ophthalmic, suppository, aerosol, topical or other similar formulations. In addition to the compounds of the invention, or a biological equivalent thereof, such pharmaceutical compositions may contain pharmaceutically-acceptable carriers and other ingredients known to enhance and facilitate drug administration.

The pharmaceutical compositions described herein can be prepared alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient. In addition to the active ingredient, a pharmaceutical composition of the invention may further comprise one or more additional pharmaceutically active agents.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and U.S. Pat. No. 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or *arachis* oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

In yet another embodiment, compositions of the invention may be administered to the desired location of a subject by a transdermal patch. A transdermal patch is meant a system capable of delivery of a compound to a subject via the skin, or any suitable external surface, including mucosal membranes, such as those found inside the mouth. Such delivery systems generally comprise a flexible backing, an adhesive and a compound retaining matrix, the backing protecting the adhesive and matrix and the adhesive holding the whole on the skin of the subject. On contact with the skin, the compound-retaining matrix delivers the compound to the skin, the compound then passing through the skin into the subject's system.

Certain embodiments of the invention provide a pharmaceutical preparation/dosage formulation provided in the form of a transdermal patch and formulated for sustained release formulation, in a therapeutically effective amount sufficient to treat a disease associated with activation of an immune cell (e.g., rheumatoid arthritis) in a patient, wherein the dosage formulation, when administered (provided as a patch) to the patient, provides a substantially sustained dose over at least about 2 hours, 4 hours, 6 hours, 8, hours, 12 hours, 20 hours, or at least about 24 hours.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, subcutaneous, intraperitoneal, intramuscular, intrastemal injection, bolus injections, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

A pharmaceutical composition of the invention may be prepared, packaged, or sold in a formulation suitable for pulmonary administration via the buccal cavity. Such a formulation may comprise dry particles that comprise the active ingredient and that have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful in pulmonary delivery are also useful in intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, contain 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Typically, dosages of the compound of the invention which may be administered to a subject, preferably a human, will vary depending upon any number of factors, including but not limited to, the type of animal and type of disease state being treated, the age of the subject and the route of administration.

The compound can be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the subject, and the like.

Kit and Probes

In some embodiments, the present invention also includes pharmaceutical kits and/or research probes useful, for example, in the treatment or prevention of HDACs associated diseases or disorders such as cancer, neurodegenerative diseases and pathological autoimmune response. In one embodiment, the kit includes a compound of the present invention. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

In some embodiments, the present invention also includes probes comprising a compound of the invention, useful, for example, in the treatment or prevention of HDACs associated diseases or disorders such as cancer, neurodegenerative diseases and pathological autoimmune response, or in the imaging or theragnostics approaches to HDACs associated diseases or disorders such as cancer, neurodegenerative diseases and pathological autoimmune response. In one embodiment, a probe comprises a compound of the invention further conjugated to a radiolabeled moiety, a fluorescent labeled moiety, or biotin. Any numbers of linkers known in the art can be used for conjugation. In another embodiment, no linker is necessary for conjugation. In some embodiments, a conjugated probe including a compound of the invention is used for research, diagnostic and therapeutic purposes.

In one aspect, the invention provides methods comprising the use of theragnostics, or theranostics, further comprising a compound of the invention. Theragnostics, or theranostics, are compounds, formulations and compositions, capable of functioning as both therapeutic agents and diagnostic agents. For example, a probe of the invention can inhibit or modulate the activity of one or more HDACs, and at the same time provide for the possibility of imaging its distribution in a cell, tissue, organ, or entire body. Modern approaches to theragnostics, or theranostics, have been described by Xie et al., 2010, Adv Drug Deliv Rev, 62(11):1064-1079, and Pene et al., 2009, Crit Care Med., 37(1 Suppl):S50-8, descriptions incorporated herein in their entirety.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The experiments disclosed herein were designed to generate novel HDACs inhibitors, both pan-inhibitors of several or all classes of HDACs, and selective inhibitors between and/or within classes. These inhibitors can serve as novel therapeutic agents for HDACs related diseases and disorders. The materials and methods employed in these experiments are now described.

Materials and Methods: Enzymes

Human HDAC1 (GenBank Accession No. NM_004964), full-length with a C-terminal His-tag and a C-terminal FLAG-tag, MW=56 kDa, was expressed in a baculovirus expression system.

Human HDAC2 (GenBank Accession No. NM_001527), full-length with a C-terminal His-tag, MW=56 kDa, was expressed in a baculovirus expression system.

Complex of human HDAC3 (GenBank Accession No. NM_003883), full-length with a C-terminal His tag, MW=49.7 kDa, and human NCOR2 (amino acid 395-489) (GenBank Accession No. NM_006312), N-terminal GST tag, MW=37.6 kDa, was co-expressed in a baculovirus expression system.

Human HDAC4 (GenBank Accession No. NM_006037), amino acids 627-1085 with a N-terminal GST tag, MW=75.2 kDa, was expressed in a baculovirus expression system.

Human HDAC5 (GenBank Accession No. NM_005474), full-length with an N-terminal GST tag, MW=150 kDa, was expressed in a baculovirus expression system.

Recombinant human HDAC6 (GenBank Accession No. BC069243), full-length, MW=180 kDa, was expressed by baculovirus in Sf9 insect cells using an N-terminal GST tag.

Human HDAC7 (GenBank Accession No. AY302468), (a.a. 518-end) with an N-terminal GST tag, MW=78 kDa, was expressed in a baculovirus expression system.

Human HDAC8 (GenBank Accession No. NM_018486), full-length with a C-terminal His tag, MW=46.4 kDa, was expressed in a baculovirus expression system.

Human HDAC9 (GenBank Accession No. NM_178423), amino acids 604-1066 with a C-terminal His tag, MW=50.7 kDa, was expressed in a baculovirus expression system.

Human HDAC10 (a.a. 1-481), GenBank Accession No. NM_032019 with a N-terminal GST tag and a C-terminal His tag, MW=78 kDa, was expressed in a baculovirus expression system.

Human HDAC11 (full length) (GenBank Accession No. NM_024827) with a N-terminal GST tag, MW=66 kDa, was expressed in a baculovirus expression system.

Human SIRT1 (Sirtuin 1, hSir2SIRT1)(GenBank Accession No. NM012238): Full length, MW=82 kDa, expressed in E. coli.

Human SIRT2 (Sirtuin 2, hSir2SIRT2)(GenBank Accession No. NM_012237): Full length, MW=43 kDa, expressed in E. coli.

Human SIRT3 (Sirtuin 3) (GenBank Accession No. NM_012239): Amino acids 102-399 (catalytically active), MW=32.7 kDa, expressed in E. coli.

Human SIRT5 (Sirtuin 5) (GenBank Accession No. NM_012241 (isoform 1); residues 37-310, MW=32.3 kDa) expressed in E. coli with an N-terminal His-tag).

The substrate RHKKAc-AMC, RHKAcKAc-AMC and AcK(trifluoroacetyl)-AMC were synthesized by Biomer.

ACY-1215, SAHA, Tubastatin A and Trichostatin A (TSA) was purchased from Selleckchem. TMP269 was purchased from MedKoo Biosciences. Nicotinamide adenine dinucleotide (NAD) was purchased from Tocris.

Materials and Methods: Biochemical Assay Procedure

I. Compound handling: Testing compounds were dissolved in 100% DMSO to a specific concentration. The serial dilution was conducted by epMotion 5070 in DMSO.
II. HDAC reaction buffer: 50 mM Tris-HCl, pH8.0, 137 mM NaCl, 2.7 mM KCl, and 1 mM MgCl2, Added fresh: 1 mg/ml BSA, 1% DMSO.
III. Substrate: Fluorogenic HDAC General Substrate for HDAC1, 2, 3, 6, 10, 11 ans Sirt1, 2 and 3: Arg-His-Lys-Lys(Ac); HDAC8 only substrate: Arg-His-Lys(Ac)-Lys(Ac); Class2A Substrate (HDAC4, 5, 7 and 9): Acetyl-Lys(trifluoroacetyl)-AMC; Sirt5 substrate: Ac-Lys(succinyl)-AMC.
IV. General Reaction Procedure: (Standard IC50 determination)
   a. Delivered 2× enzyme in wells of reaction plate except No Enzyme (No En) control wells. Add buffer in No En wells.
   b. Delivered compounds in 100% DMSO into the enzyme mixture by Acoustic technology (Echo550; nanoliter range). Spin down and pre-incubation.
   c. Delivered 2× Substrate Mixture (Fluorogenic HDAC Substrate and co-factor (500 µM of Nicotinamide adenine dinucleotide ($NAD^+$) in all Sirt assay) in all reaction wells to initiate the reaction. Spin and shake.
   d. Incubated for 1-2 hr. at 30° C. with seal.
   e. Added Developer with Trichostatin A (or TMP269 or $NAD^+$) to stop the reaction and to generate fluorescent color.
   f. Fluorescence was read (excitatory, 360; emission, 460) using the EnVision Multilabel Plate Reader (Perkin Elmer)
   g. Endpoint reading was taken for analysis after the development reaches plateau.
V. Data Analysis: The percentages of enzyme activity (relative to DMSO controls) and IC50 values were calculated using the GraphPad Prism 4 program based on a sigmoidal dose-response equation.

Example 1

Figure 2:
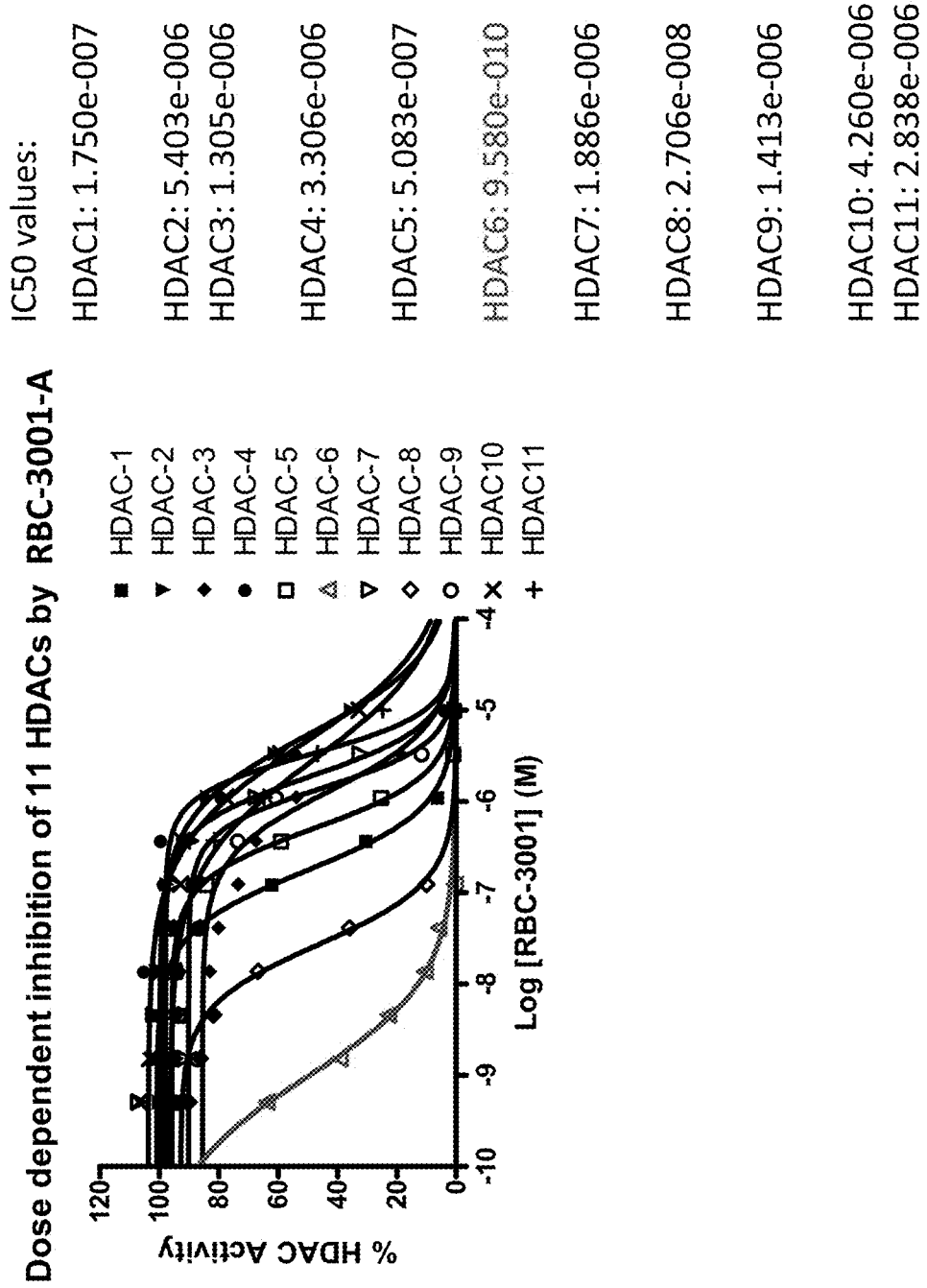
FIG. 2 depicts the results of an exemplary experiment assessing the inhibitory activities of RBC-3001-A in biochemical HDAC assays. RBC-3001-A with indicated doses was tested in the biochemical assays of HDAC1, HDAC2, HDAC3, HDAC4, HDAC5, HDAC6, HDAC7, HDAC8, HDAC9, HDAC10, or HDAC11 enzyme. The curve fit and IC50 values were calculated using the GraphPad Prism 4 program based on a sigmoidal dose-response equation.

Dose Dependent Inhibition of 11 HDACs by RBC-3001-A in Enzymatic Assays, and IC50 Values of RBC-3001-A and Reference Compounds in HDAC Enzymatic Assays The inhibitory activities of RBC-3001-A was determined using biochemical HDAC assays as depicted in FIG. 2. RBC-3001-A with indicated doses was tested in the biochemical assays of HDAC1, HDAC2, HDAC3, HDAC4, HDAC5, HDAC6, HDAC7, HDAC8, HDAC9, HDAC10, or HDAC11 enzyme. The curve fit and IC50 values were calculated using the GraphPad Prism 4 program based on a sigmoidal dose-response equation. Table 1 shows the IC50 values of RBC-3001-A and reference compounds in the HDAC Enzymatic Assays.

TABLE 1

| Compound ID | HDAC1 IC50 (M) | HDAC2 IC50 (M) | HDAC3 IC50 (M) | HDAC4 IC50 (M) | HDAC5 IC50 (M) | HDAC6 IC50 (M) | HDAC7 IC50 (M) | HDAC8 IC50 (M) | HDAC9 IC50 (M) | HDAC10 IC50 (M) | HDAC11 IC50 (M) |
|---|---|---|---|---|---|---|---|---|---|---|---|
| RBC-3001-A | 1.75E-07 | 5.40E-06 | 1.31E-06 | 3.31E-06 | 5.08E-07 | 9.58E-10 | 1.89E-06 | 2.71E-08 | 1.41E-06 | 4.26E-06 | 2.84E-06 |
| Trichostatin A | 1.03E-08 | 2.07E-08 | 2.99E-08 | 5.78E-06 | 3.53E-06 | 1.05E-09 | 4.29E-06 | 4.72E-07 | 6.93E-06 | 3.00E-08 | 2.39E-08 |
| SAHA | 2.93E-07 | 6.83E-07 | 4.35E-07 | 2.74E-05 | 1.22E-05 | 1.77E-08 | >1.0e-05 | 1.13E-06 | >1.0e-05 | 6.04E-07 | 5.97E-07 |
| TMP269 | >1.0e-05 | >1.0e-05 | >1.0e-05 | 2.13E-07 | 6.57E-08 | >1.0e-05 | 3.24E-08 | >1.0e-05 | 1.29E-08 | >1.0e-05 | >1.0e-05 |

Example 2

Figure 3:
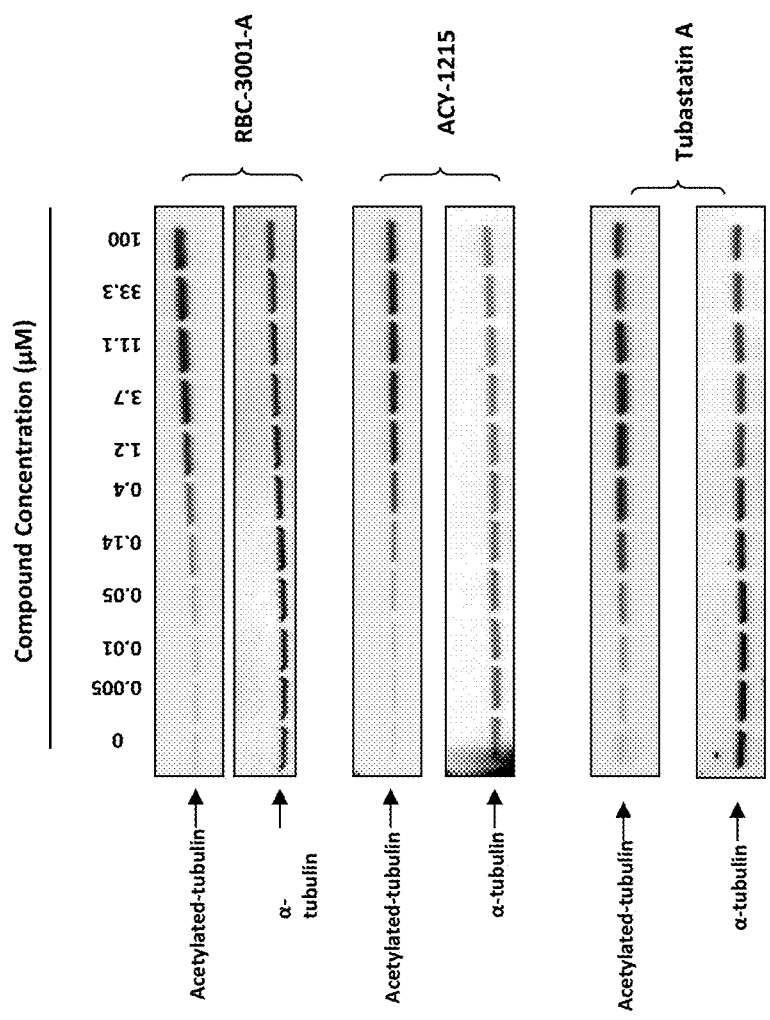
FIG. 3 depicts the modulation of α-Tubulin acetylation by compound RBC-3001-A and reference compounds ACY-1215 and Tubastatin A in PC-3 cells. PC-3 cells were treated with the indicated concentrations of RBC-3001-A for 24 hours. The whole cell lysates were subjected to Western blot analyses with anti-Acetylated-tubulin antibody. The blots were then re-probed with anti-alpha-tubulin antibody.

Modulation of a-Tubulin Acetylation by Compound RBC-3001-A and Reference Compounds in PC-3 Cells PC-3 cells were treated with the indicated concentrations of RBC-3001-A for 24 hours as depicted in FIG. 3. The whole cell lysates were subjected to Western blot analyses with anti-Acetylated-tubulin antibody. The blots were then re-probed with anti-alpha-tubulin antibody.

Example 3

IC50 Values of RBC-3001-B, and Reference Compounds in HDAC Enzymatic Assays

The inhibitory activities of RBC-3001-B were determined using biochemical HDAC assays similar to those used for determining the inhibitory activities of RBC-3001-A. FIG. 4 includes a table showing the IC50 values of RBC-3001-B, and reference compounds in the HDAC Enzymatic Assays.

Example 4

Figure 5:
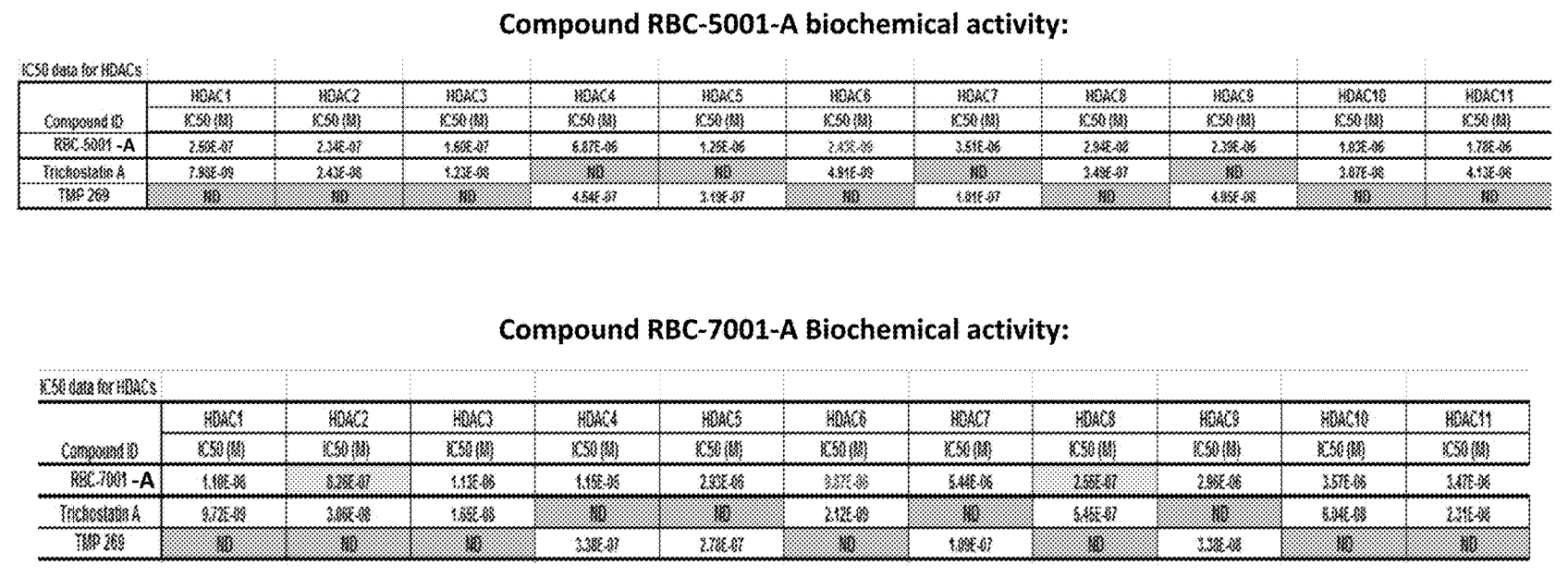

IC50 Values of RBC-5001-A, RBC-7001-A, and Reference Compounds in HDAC Enzymatic Assays The inhibitory activities of RBC-5001 and RBC-7001 were determined using biochemical HDAC assays similar to those used for determining the inhibitory activities of RBC-3001. FIG. 5 includes two tables showing the IC50 values of RBC-5001, RBC-7001, and reference compounds in the HDAC Enzymatic Assays.

The disclosures of each and every patent, patent application, and publication cited herein are hereby incorporated herein by reference in their entirety. While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound selected from the group consisting of Formulae VI-A, VII-A, VIII-A, IX-A, X-A, VI-B, VII-B, VIII-B, IX-B, and X-B, or a salt or solvate thereof:

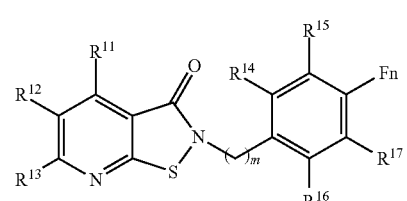
Formula VI-A

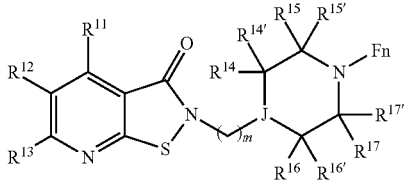
Formula VII-A

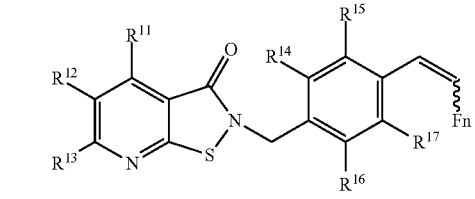
Formula VIII-A

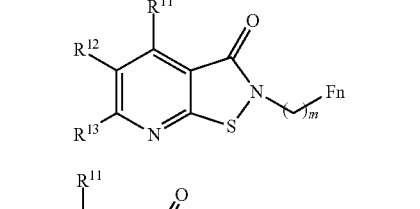
Formula IX-A

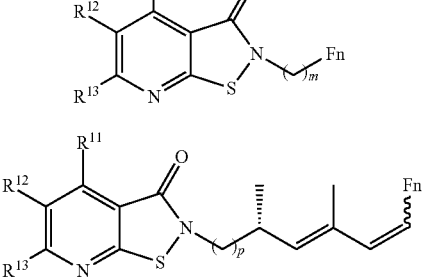
Formula X-A

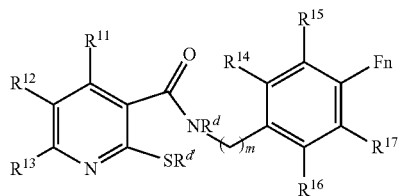
Formula VI-B

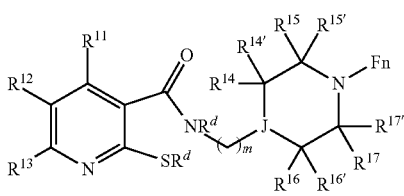
Formula VII-B

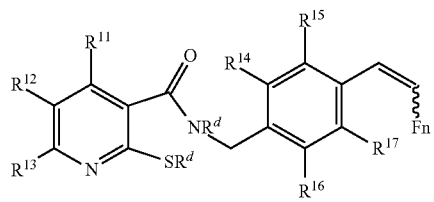
Formula VIII-B

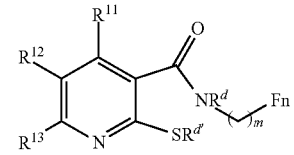
Formula IX-B

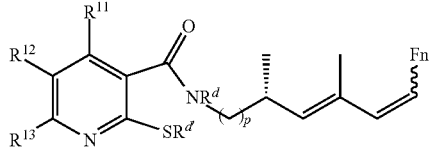
Formula X-B wherein in Formulae VI-A to X-B:
$R^{11}$, $R^{12}$, $R^{13}$, $R^{14}$, $R^{14'}$, $R^{15}$, $R^{15'}$, $R^{16}$, $R^{16'}$, $R^{17}$ and $R^{17'}$ are each independently selected from the group consisting of H, F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, and wherein $R^d$, $R^{d'}$, $R^e$ and $R^f$ are each independently selected from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of $R^d$, $R^{d'}$, $R^e$ or $R^f$ can optionally be joined to form additional rings; and any of $R^{11}$, $R^{12}$, $R^{13}$, $R^{14}$, $R^{14'}$, $R^{15}$, $R^{15'}$, $R^{16}$, $R^{16'}$, $R^{17}$, and $R^{17'}$ can optionally be connected to each other to form various carbo- or heterocyclic rings;

m is an integer from 0 to 3, n is an integer from 0 to 7 and p is an integer from 0 to 2;

J is selected from the group consisting of CH and N; and

Fn is selected from the group consisting of Formulae II, III, IV and V:

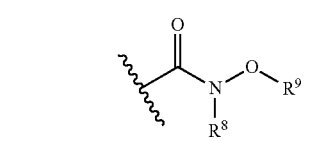

Formula II

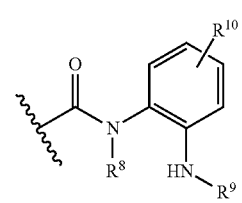

Formula III

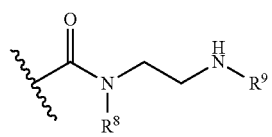

Formula IV

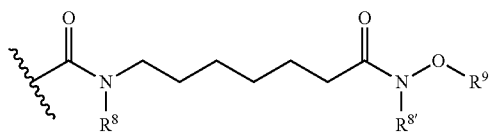

Formula V wherein in Formulae II, III, IV and V:

$R^8$, $R^{8'}$, $R^9$, and $R^{10}$ are each independently selected from the group consisting of H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and $R^{10}$ can represent single, multiple, or no substitution.

2. The compound of claim 1, wherein the compound has a chemical structure selected from the group consisting of N-(2-amino-4-(thiophen-2-yl)phenyl)-4-((3-oxoisothiazolo[5,4-b]pyridin-2(3H)-yl)methyl)benzamide, N-(2-amino-5-(thiophen-2-yl)phenyl)-4-((3-oxoisothiazolo[5,4-b]pyridin-2(3H)-yl)methyl)benzamide, N-hydroxy-4((3-oxoisothiazolo[5,4-b]pyridin-2(3H)-yl)methyl)benzamide, N-(7-(hydroxyamino)-7-oxoheptyl)-4-((3-oxoisothiazolo[5,4-b]pyridin-2(3H)-yl)methyl)benzamide, N-(2-aminophenyl)-4((3-oxoisothiazolo[5,4-b]pyridin-2(3H)-yl)methyl)benzamide, N-(4-((2-amino-4-(thiophen-2-yl)phenyl)carbamoyl)benzyl)-2-mercaptonicotinamide, N-(4-((2-amino-5-(thiophen-2-yl)phenyl)carbamoyl)benzyl)-2-mercaptonicotinamide, N-(4-(hydroxycarbamoyl)benzyl)-2-mercaptonicotinamide, N-(4-((7-(hydroxyamino)-7-oxoheptyl)carbamoyl)benzyl)-2-mercaptonicotinamide, and N-(4-((2-aminophenyl)carbamoyl)benzyl)-2-mercaptonicotinamide, or a pharmaceutically acceptable salt thereof.

3. A composition comprising the compound of claim 1, or a salt or solvate thereof, and at least one pharmaceutically acceptable carrier.

4. A method of inhibiting HDAC in a subject, the method comprising administering to the subject a therapeutically effective amount of a compound of Formulae VI-A, VII-A, VIII-A, IX-A, X-A, VI-B, VII-B, VIII-B, IX-B, and X-B, or a salt or solvate thereof:

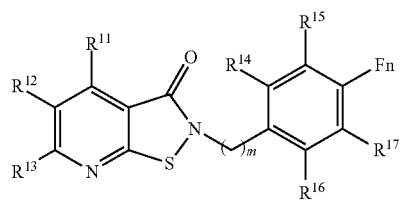

Formula VI-A

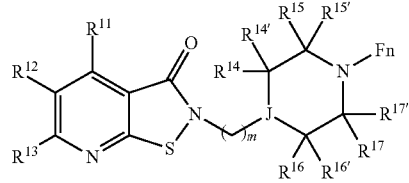

Formula VII-A

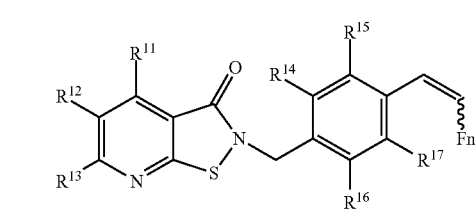

Formula VIII-A

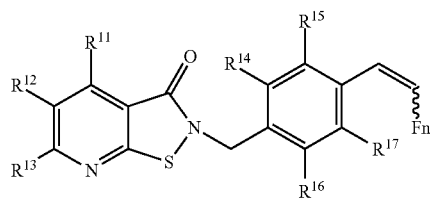

Formula IX-A

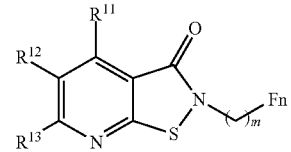

Formula X-A

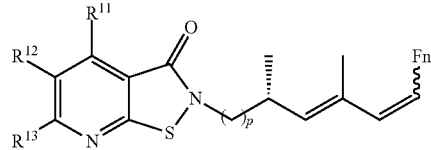

Formula VI-B

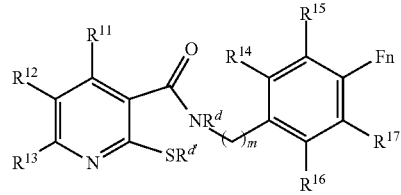

Formula VII-B

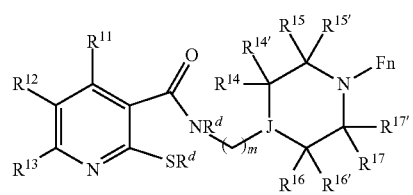

-continued

Formula VIII-B

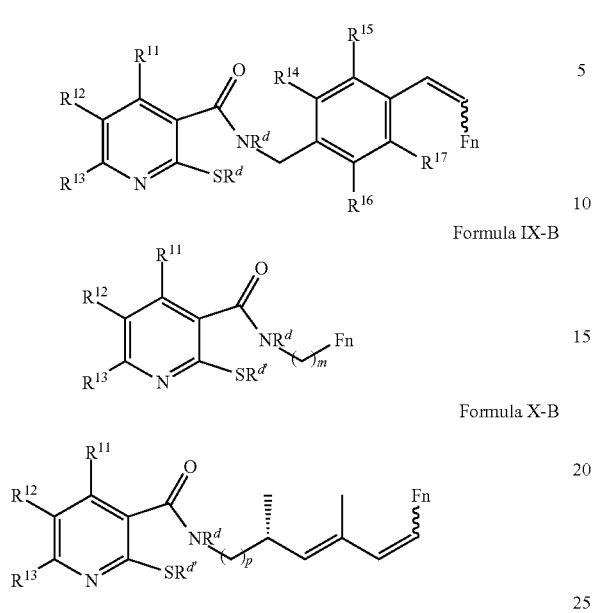

Formula IX-B

Formula X-B

Formula II

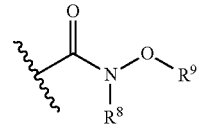

Formula III

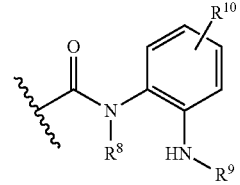

Formula IV

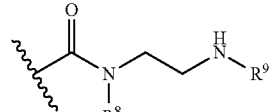

Formula V

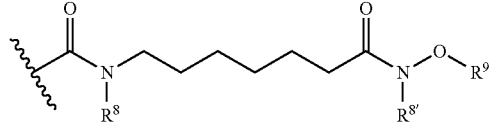

wherein in Formulae VI-A to X-B:

$R^{11}$, $R^{12}$, $R^{13}$, $R^{14}$, $R^{14'}$, $R^{15}$, $R^{15'}$, $R^{16}$, $R^{16'}$, $R^{17}$ and $R^{17'}$ are each independently selected from the group consisting of H, F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, and wherein $R^d$, $R^{d'}$, $R^e$ and $R^f$ are each independently selected from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of $R^d$, $R^{d'}$, $R^e$ or $R^f$ can optionally be joined to form additional rings; and any of $R^{11}$, $R^{12}$, $R^{13}$, $R^{14}$, $R^{14'}$, $R^{15}$, $R^{15'}$, $R^{16}$, $R^{16'}$, $R^{17}$, and $R^{17'}$ can optionally be connected to each other to form various carbo- or heterocyclic rings;

m is an integer from 0 to 3, n is an integer from 0 to 7 and p is an integer from 0 to 2;

J is selected from the group consisting of CH and N; and

Fn is selected from the group consisting of Formulae II, III, IV and V:

wherein in Formulae II, III, IV and V:

$R^8$, $R^{8'}$, $R^9$, and $R^{10}$ are each independently selected from the group consisting of H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and $R^{10}$ can represent single, multiple, or no substitution.

5. The method of claim 4 wherein the compound has a chemical structure selected from the group consisting of N-(2-amino-4-(thiophen-2-yl)phenyl)-4-((3-oxoisothiazolo[5,4-b]pyridin-2(3H)-yl)methyl)benzamide, N-(2-amino-5-(thiophen-2-yl)phenyl)-4-((3-oxoisothiazolo[5,4-b]pyridin-2(3H)-yl)methyl)benzamide, N-hydroxy-4-((3-oxoisothiazolo[5,4-b]pyridin-2(3H)-yl)methyl)benzamide, N-(7-(hydroxyamino)-7-oxoheptyl)-4-((3-oxoisothiazolo[5,4-b]pyridin-2(3H)-yl)methyl)benzamide, N-(2-aminophenyl)-4((3-oxoisothiazolo[5,4-b]pyridin-2(3H)-yl)methyl) benzamide, N-(4-((2-amino-4-(thiophen-2-yl)phenyl) carbamoyl)benzyl)-2-mercaptonicotinamide, N-(4-((2-amino-5-(thiophen-2-yl)phenyl)carbamoyl)benzyl)-2-mercaptonicotinamide, N-(4-(hydroxycarbamoyl)benzyl)-2-mercaptonicotinamide, N-(4-((7-(hydroxyamino)-7-oxoheptyl)carbamoyl)benzyl)-2-mercaptonicotinamide, and N-(4-((2-aminophenyl)carbamoyl)benzyl)-2-mercaptonicotinamide, or a pharmaceutically acceptable salt thereof, or a pharmaceutically acceptable salt thereof.

6. The method of claim 4, wherein the compound selectively inhibits an HDAC selected from the group consisting of HDAC1, HDAC2, HDAC3, HDAC4, HDAC5, HDAC6, HDAC7, HDAC8, HDAC9, HDAC10, HDAC11, SIRT1, SIRT2, SIRT3, SIRT4, SIRT5, SIRT6, and SIRT7.

7. The method of claim 4, wherein the compound selectively inhibits HDAC6.

8. The method of claim 4, wherein the compound selectively inhibits HDAC8.

9. The method of claim 4, wherein the subject is a human.

10. The method of claim 4, wherein the subject has cancer.

11. The method of claim 4, wherein the subject has a disease or disorder is selected from the group consisting of a psychiatric disease or disorder, a neurologic disease or disorder, a neurodegenerative disease or disorder, and a neuroinflammation disease or disorder.

12. The method of claim 4 wherein the compound is administered to the subject orally, parenterally, intravascularly, intranasally, or intrabronchially.

13. The method of claim 4, further comprising:
    administering to the subject a therapeutically effective amount of an additional therapeutic agent for the treatment of a disease or disorder.

14. The method of claim 13, wherein the additional therapeutic agent is selected from the group consisting of an immunomodulatory drug, an immunotherapeutic drug, a DNA-damaging chemotherapeutic, a proteasome inhibitor, an anti-androgen receptor, an antiretroviral drug, a reverse-transcriptase inhibitor, a chemotherapeutic drug, and an immunosuppressant.

* * * * *